(12) United States Patent
Clopp

(10) Patent No.: US 10,779,891 B2
(45) Date of Patent: Sep. 22, 2020

(54) SYSTEM AND METHOD FOR NAVIGATION OF SURGICAL INSTRUMENTS

(71) Applicant: Acclarent, Inc., Menlo Park, CA (US)

(72) Inventor: Mathew D. Clopp, Santa Clara, CA (US)

(73) Assignee: Acclarent, Inc., Irvine, CA (US)

( * ) Notice: Subject to any disclaimer, the term of this patent is extended or adjusted under 35 U.S.C. 154(b) by 1355 days.

(21) Appl. No.: 14/927,924

(22) Filed: Oct. 30, 2015

(65) Prior Publication Data

US 2017/0119473 A1    May 4, 2017

(51) Int. Cl.
*A61B 34/20* (2016.01)
*A61B 17/24* (2006.01)
(Continued)

(52) U.S. Cl.
CPC .............. *A61B 34/20* (2016.02); *A61B 5/062* (2013.01); *A61B 17/24* (2013.01); *A61B 17/8897* (2013.01); *A61F 11/002* (2013.01); *A61M 25/09* (2013.01); *A61M 29/02* (2013.01); *A61B 90/361* (2016.02); *A61B 2017/246* (2013.01); *A61B 2034/2051* (2016.02); *A61B 2034/2072* (2016.02); *A61B 2090/306* (2016.02); *A61B 2090/365* (2016.02); *A61M 2025/09083* (2013.01); *A61M 2025/09125* (2013.01); *A61M 2029/025* (2013.01); *A61M 2210/0681* (2013.01)

(58) Field of Classification Search
CPC ..... A61B 34/20; A61B 17/8897; A61B 17/24; A61B 5/062; A61B 2090/365; A61B 2090/306; A61B 2090/361; A61B 2090/25; A61B 2034/2072; A61B 2034/2051; A61B 2017/246; A61M 29/02; A61M 25/09; A61M 25/10; A61M 25/0105; A61M 2210/0681; A61M 2025/09125; A61M 2025/09083; A61F 11/002

See application file for complete search history.

(56) References Cited

U.S. PATENT DOCUMENTS 5,178,159 A    1/1993    Christian
5,348,481 A *  9/1994    Ortiz .................. H01R 24/58
                                                439/25
(Continued)

OTHER PUBLICATIONS

International Search Report and Written Opinion dated Apr. 18, 2017 for Application No. PCT/US2016/058736, 18 pgs.
(Continued)

*Primary Examiner* — Boniface N Nganga
(74) *Attorney, Agent, or Firm* — Frost Brown Todd LLC

(57) ABSTRACT

An apparatus includes a navigational guidewire and a connector assembly. The navigational guidewire includes a sensing element, an outer member, and a conductor. The sensing element is configured to respond to positioning within an electromagnetic field. The conductor is in communication with the sensing element. The connector assembly is configured to couple the navigational guidewire with a navigation system. The connector assembly includes a body and a ferrule. The ferrule is coupled with the body. The navigational guidewire is coupled with the ferrule. The ferrule is rotatable relative to the body to thereby enable rotation of the navigational guidewire relative to the body.

20 Claims, 18 Drawing Sheets

(51) Int. Cl.
*A61B 5/06* (2006.01)
*A61M 25/09* (2006.01)
*A61B 17/88* (2006.01)
*A61F 11/00* (2006.01)
*A61M 29/02* (2006.01)
*A61B 90/00* (2016.01)
*A61B 90/30* (2016.01)

(56) References Cited

U.S. PATENT DOCUMENTS

| | | | |
|---|---|---|---|
| 6,016,439 | A | 1/2000 | Acker |
| 7,720,521 | B2 | 5/2010 | Chang et al. |
| 8,123,722 | B2 | 2/2012 | Chang et al. |
| 8,190,389 | B2 | 5/2012 | Kim et al. |
| 8,320,711 | B2 | 11/2012 | Altmann et al. |
| 8,702,626 | B1 | 4/2014 | Kim et al. |
| 9,155,492 | B2 | 10/2015 | Jenkins et al. |
| 9,167,961 | B2 | 10/2015 | Makower et al. |
| 9,198,736 | B2 | 12/2015 | Kim et al. |
| 9,226,800 | B2 | 1/2016 | Burg et al. |
| 9,408,955 | B2 | 8/2016 | Jenkins et al. |
| 2003/0009190 | A1* | 1/2003 | Kletschka ........ A61B 17/22032 606/200 |
| 2004/0097804 | A1 | 5/2004 | Sobe |
| 2004/0162465 | A1 | 8/2004 | Carrillo |
| 2006/0004286 | A1* | 1/2006 | Chang .................... A61B 34/20 600/435 |
| 2006/0074318 | A1* | 4/2006 | Ahmed ............... A61B 5/02158 600/465 |
| 2007/0208252 | A1 | 9/2007 | Makower |
| 2008/0082045 | A1* | 4/2008 | Goldfarb ............ A61B 1/00126 604/96.01 |
| 2008/0091177 | A1* | 4/2008 | Christian ............. A61B 5/0031 606/1 |
| 2008/0183128 | A1 | 7/2008 | Morriss et al. |
| 2010/0030031 | A1 | 2/2010 | Goldfarb et al. |
| 2010/0168511 | A1* | 7/2010 | Muni ................. A61M 25/0152 600/104 |
| 2011/0004057 | A1 | 1/2011 | Goldfarb et al. |
| 2011/0060214 | A1 | 3/2011 | Makower |
| 2013/0066358 | A1* | 3/2013 | Nalluri ................. A61F 11/002 606/199 |
| 2014/0074141 | A1 | 3/2014 | Johnson et al. |
| 2014/0200444 | A1* | 7/2014 | Kim ................ A61M 25/09041 600/424 |
| 2014/0364725 | A1 | 12/2014 | Makower |
| 2015/0003789 | A1 | 1/2015 | Webler et al. |
| 2016/0008083 | A1 | 1/2016 | Kesten et al. |
| 2016/0310041 | A1 | 10/2016 | Jenkins et al. |
| 2016/0310042 | A1 | 10/2016 | Kesten et al. |

OTHER PUBLICATIONS

Chinese Office Action and Search Report dated May 18, 2020 for Application No. 201680064054.1, 10 pages.
Extended European Search Report dated Jun. 3, 2020 for Application No. 20159238.3, 7 pages.

* cited by examiner

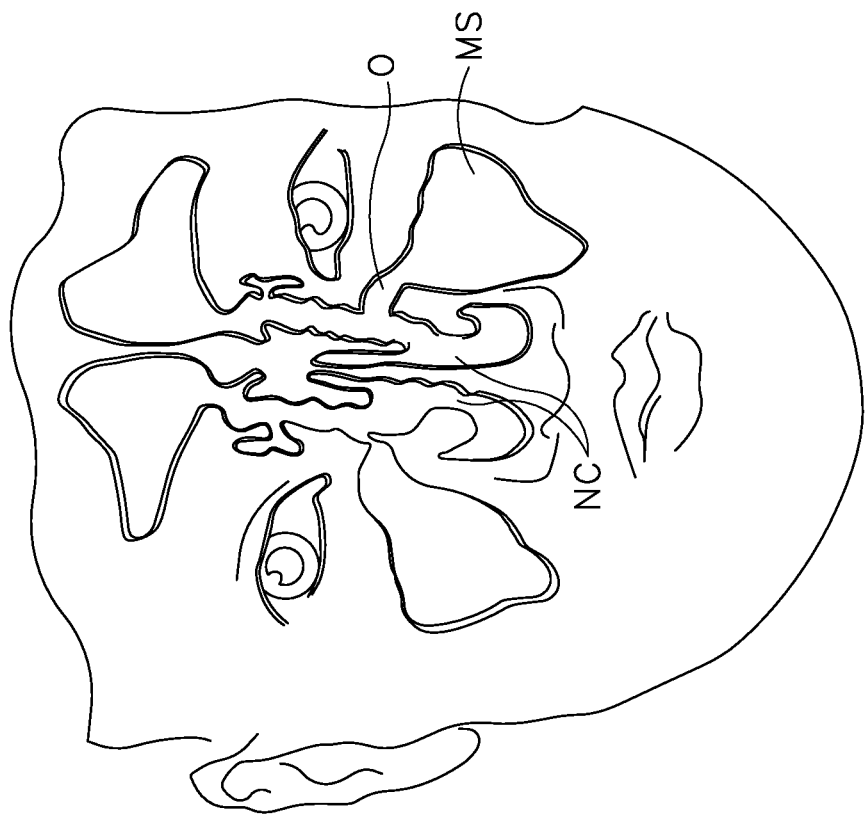
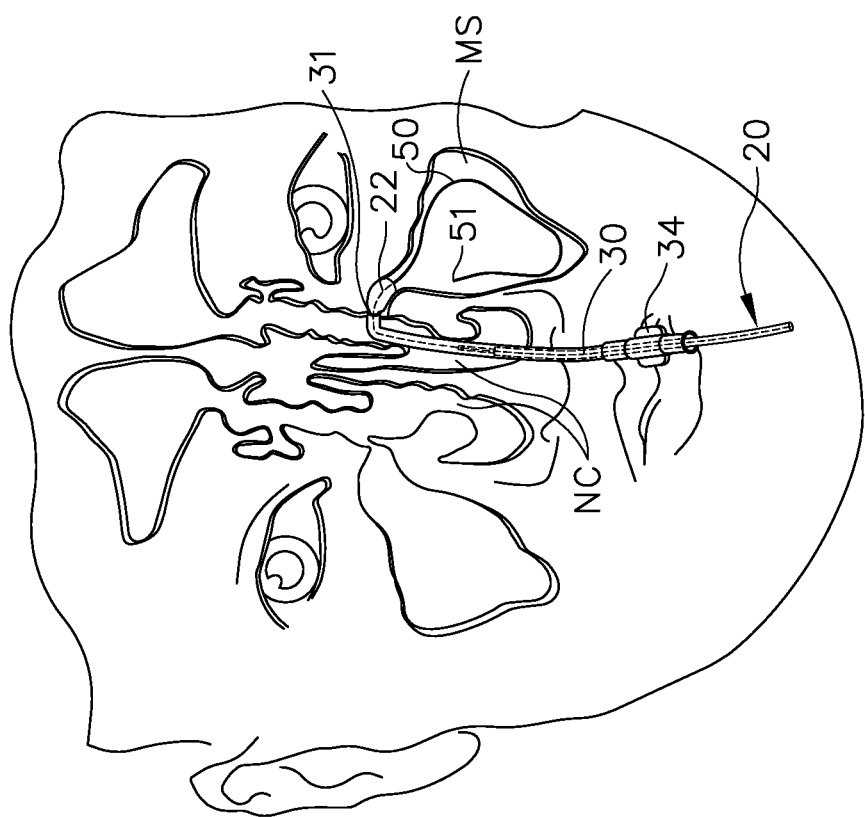

SYSTEM AND METHOD FOR NAVIGATION OF SURGICAL INSTRUMENTS

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, the disclosure of which is incorporated by reference herein. An example of such an illuminating guidewire is the Relieva Luma Sentry™ Sinus Illumination System by Acclarent, Inc. of Menlo Park, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty such as the procedure described above, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3 dimensional view of all of the anatomy surrounding the operative field, not just that which is actually visible in the spatially limited, 2 dimensional, direct line-of-sight endoscopic view. As a result, image guidance systems may be particularly useful during performance of FESS, balloon sinuplasty, and/or other ENT procedures, especially in cases where normal anatomical landmarks are not present or are difficult to visualize endoscopically.

It may be desirable to provide features that further facilitate the use of an IGS navigation system and associated components in ENT procedures and other medical procedures. While several systems and methods have been made and used with respect to IGS and ENT surgery, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2D depicts a front view of the guide catheter of FIG. 2A positioned adjacent an ostium of the maxillary sinus, with the dilation catheter of FIG. 2B translated distally relative to the guide catheter along the illuminating guidewire of FIG. 2B so as to position a balloon of the dilation catheter within the ostium;

FIG. 2E depicts a front view of an ostium of the maxillary sinus, with the ostium having been enlarged by inflation of the balloon of FIG. 2D;

Figure 1:
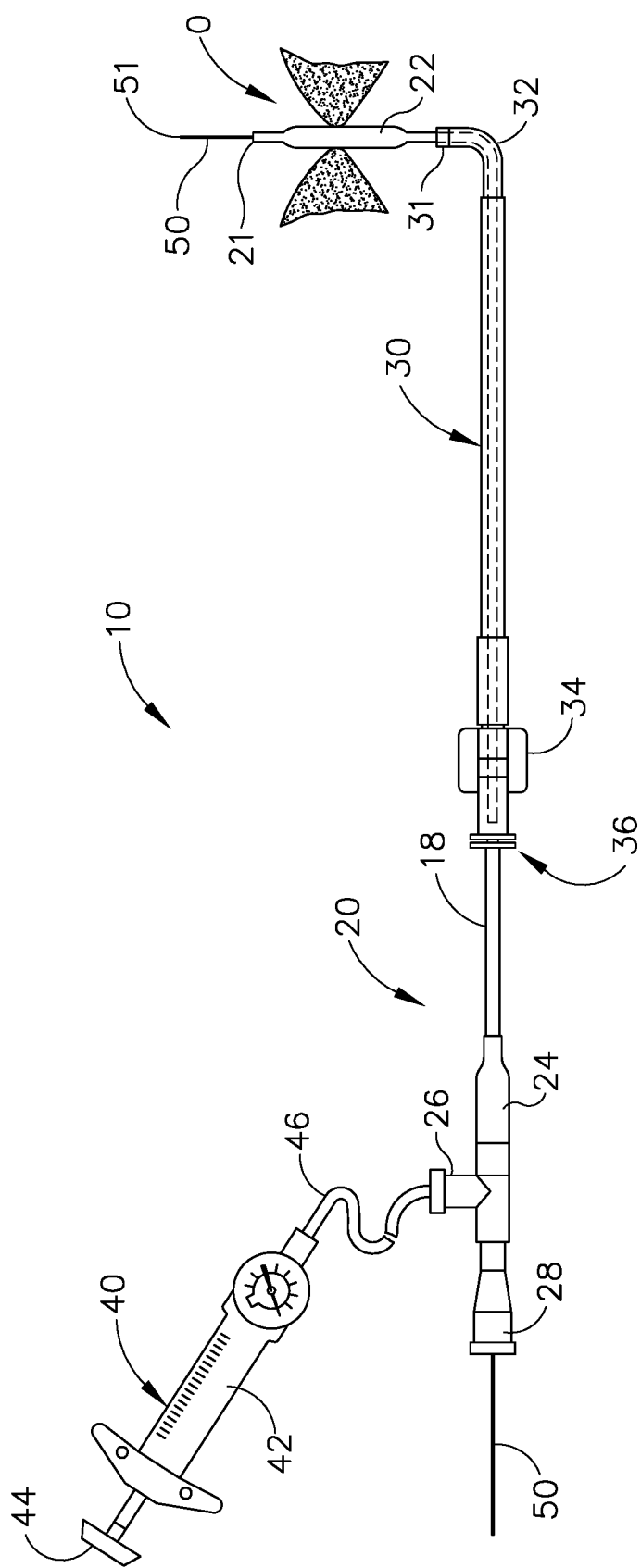
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY DILATION CATHETER SYSTEM

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end (21) of dilation catheter (20) includes an inflatable dilator (22). The proximal end of dilation catheter (20) includes a grip (24), which has a lateral port (26) and an open proximal end (28). A hollow, elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal portion (32) at its distal end (31) and a grip (34) at its proximal end. Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, the disclosure of which is incorporated by reference herein.

Guidewire (50) may take various forms. In some versions, the distal end (51) of guidewire (50) includes an illuminating element that is in optical communication with one or more illumination fibers that extend along the length of guidewire (50). By way of example only, such an illuminating version of guidewire (50) may be constructed and operable in accordance with at least some of the teachings of U.S. Pub. No. 2012/0078118, the disclosure of which is incorporated by reference herein. Similarly, guidewire (50) may be configured and operable like the Relieva Luma Sentry™ Sinus Illumination System by Acclarent, Inc. of Menlo Park, Calif. As yet another merely illustrative example, guidewire (50) may include a coil or some other kind of feature (e.g., sensor) that is configured to cooperate with a navigational system as described in greater detail below. It should be understood that some versions of guidewire (50) may include both an illuminating element and a feature that is configured to cooperate with a navigational system as described in greater detail below.

In some instances, an endoscope (not shown) is used to provide visualization within an anatomical passageway (e.g., within the nasal cavity, etc.) during a process of using dilation catheter system (10). By way of example only, such an endoscope may be configured and operable in accordance with at least some of the teachings of U.S. Pub. No. 2010/0030031, the disclosure of which is incorporated by reference herein. Similarly, such an endoscope may be configured and operable like the Acclarent Cyclops™ Multi-Angle Endoscope by Acclarent, Inc. of Menlo Park, Calif. Other suitable forms that an endoscope may take will be apparent to those of ordinary skill in the art in view of the teachings herein. It should also be understood that an endoscope may be used in combination with a navigational system as described in greater detail below to guide use of dilation catheter system (10). Alternatively, an endoscope may be used without a navigational system as described in greater detail below to guide use of dilation catheter system (10). In addition, a navigational system as described in greater detail below may be used without an endoscope to guide use of dilation catheter system (10).

FIGS. 2A-2E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 2A:
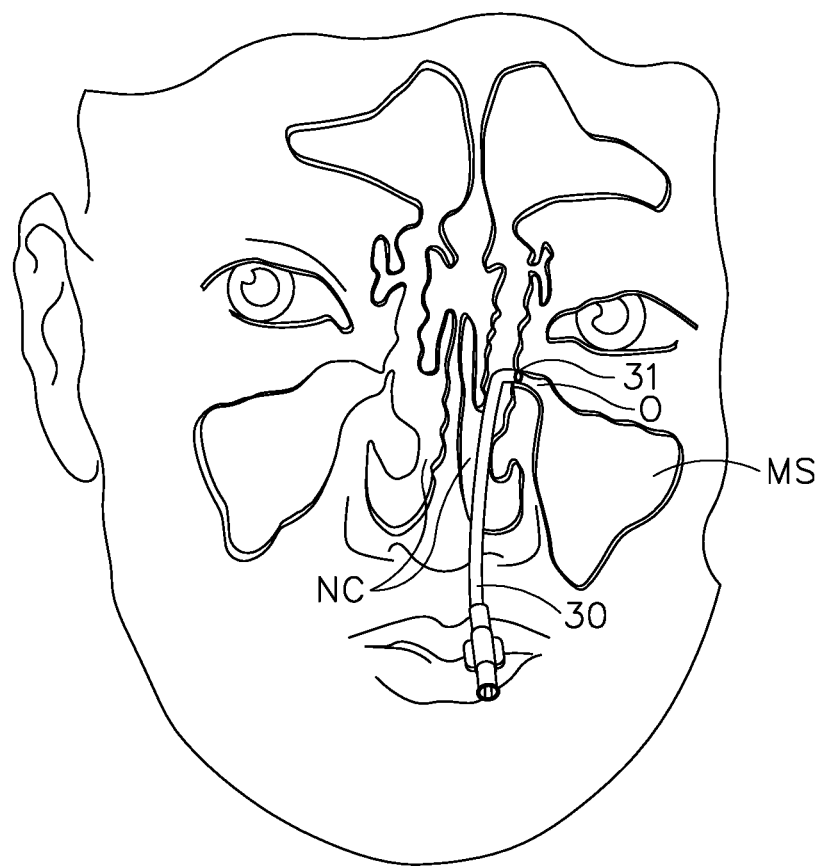
FIG. 2A depicts a front view of a guide catheter of the dilation catheter system of FIG. 1 positioned adjacent an ostium of the maxillary sinus.
Figure 2C:
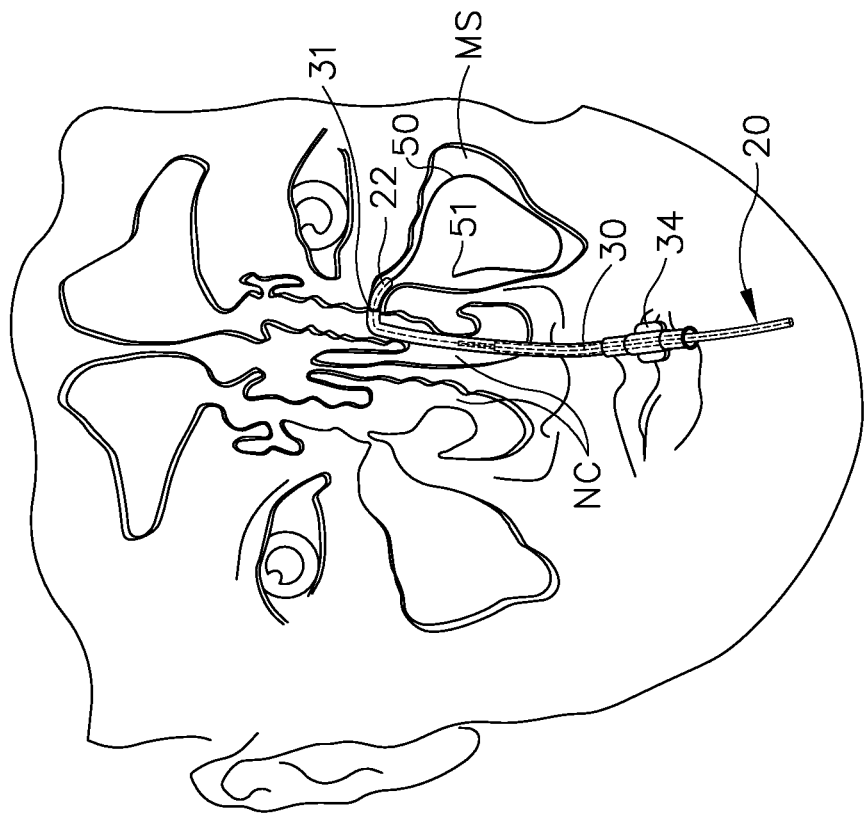
FIG. 2C depicts a front view of the guide catheter of FIG. 2A positioned adjacent an ostium of the maxillary sinus, with the illuminating guidewire of FIG. 2B translated further distally relative to the guide catheter and into the maxillary sinus.
Figure 2B:
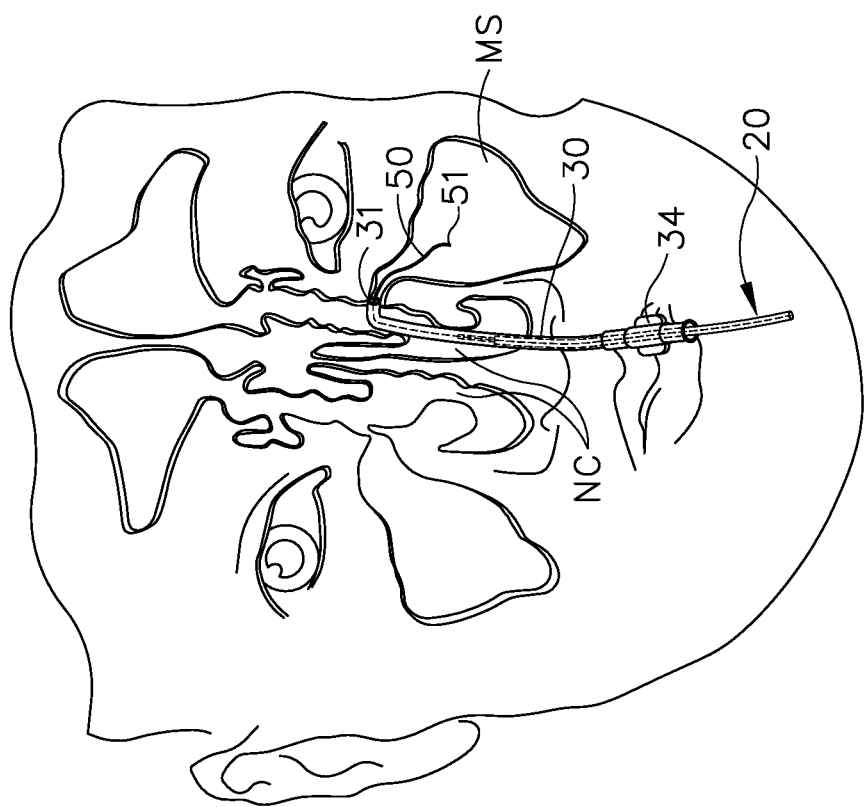
FIG. 2B depicts a front view of the guide catheter of FIG. 2A positioned adjacent an ostium of the maxillary sinus, with a dilation catheter of the dilation catheter system of FIG. 1 and an illuminating guidewire of the dilation catheter system of FIG. 1 positioned in the guide catheter and a distal portion of the guidewire positioned in the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 2A. Inflatable dilator (22) and distal end (51) of guidewire (50) may be positioned within or proximal to bent distal end (32) of guide catheter (30) at this stage. This positioning of guide catheter (30) may be verified endoscopically with an endoscope and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 2B and 2C. If guidewire (50) is an illuminating guidewire (50), the operator may illuminate guidewire (50) at this stage, which may provide transcutaneous illumination through the patient's face to enable the operator to visually confirm positioning of the distal end (51) of guidewire (50) in the maxillary sinus (MS) with relative ease.

As shown in FIG. 2C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 2D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 2E.

In some instances, it may be desirable to irrigate the sinus and paranasal cavity after dilation catheter (20) has been used to dilate the ostium (O). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pat. Pub. No. 2008/0183128, entitled "Methods, Devices and Systems for Treatment and/or Diagnosis of Disorders of the Ear, Nose and Throat," published Jul. 31, 2008. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

II. EXEMPLARY IMAGE GUIDED SURGERY NAVIGATION SYSTEM

Figure 3:
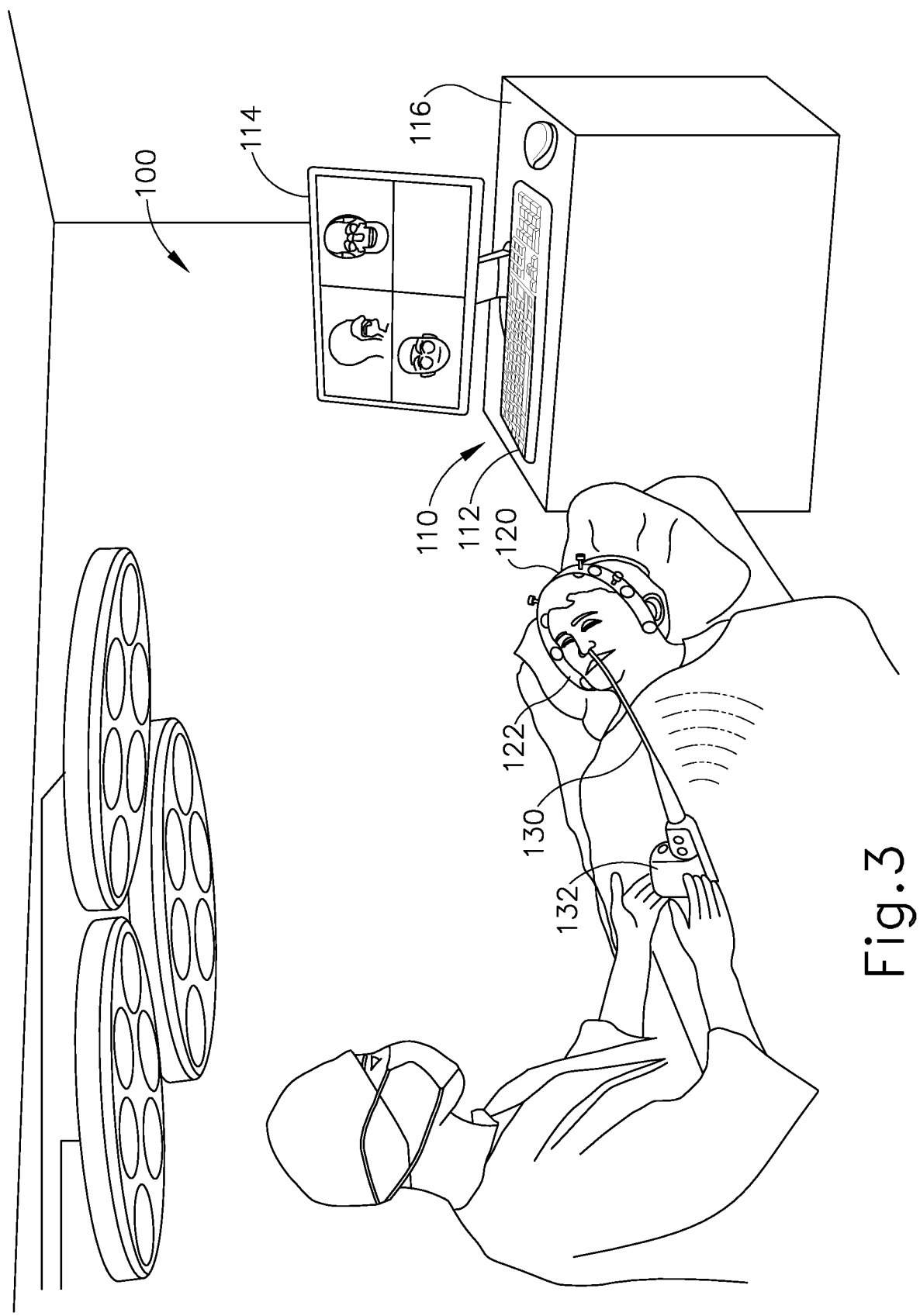
FIG. 3 depicts a schematic view of an exemplary sinus surgery navigation system.

FIG. 3 shows an exemplary IGS navigation system (100) whereby an ENT procedure may be performed using IGS. In some instances, IGS navigation system (100) is used during a sinuplasty procedure on the patient (e.g., using dilation catheter system (10) described above). However, it should be understood that IGS navigation system (100) may be readily used in various other kinds of procedures.

In addition to or in lieu of having the components and operability described herein, dilation catheter system (10) and/or IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, dilation catheter system (10) and/or IGS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, the disclosure of which is incorporated by reference herein; U.S. Pat. Pub. No. 2014/0200444, entitled "Guidewires for Performing Image Guided Procedures," published Jul. 17, 2014, the disclosure of which is incorporated by reference herein; U.S. Pat. Pub. No. 2012/0245456, entitled "Adapter for Attaching Electromagnetic Image Guidance Components to a Medical Device," published Sep. 27, 2012, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, the disclosure of which is incorporated by reference herein; U.S. Pat. Pub. No. 2008/0281156, entitled "Methods and Apparatus for Treating Disorders of the Ear Nose and Throat," published Nov. 13, 2008, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, the disclosure of which is incorporated by reference herein.

Figure 4:
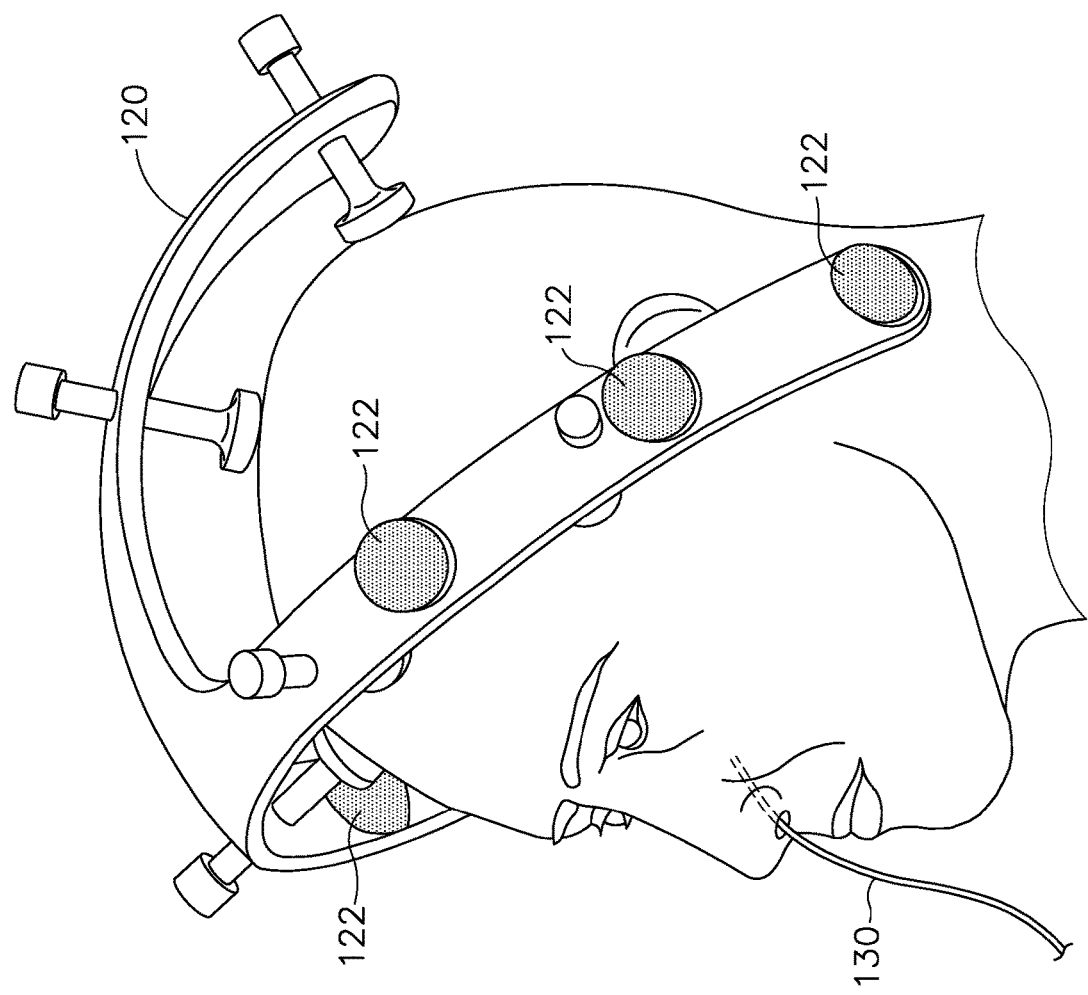
FIG. 4 depicts a perspective view of the head of a patient, with components of the navigation system of FIG. 3.

IGS navigation system (100) of the present example comprises a set of magnetic field generators (122). Before a surgical procedure begins, field generators (122) are fixed to the head of the patient. As best seen in FIG. 4, field generators (122) are incorporated into a frame (120), which is clamped to the head of the patient. While field generators (122) are secured to the head of the patient in this example, it should be understood that field generators (122) may instead be positioned at various other suitable locations and on various other suitable structures. By way of example only, field generators (122) may be mounted on an independent structure (e.g., as described below with reference to FIGS. 9-10) that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130) that is inserted into a nasal sinus of the patient and in other locations within the patient's head. In some instances, navigation guidewire (130) is used in place of guidewire (50) described above. In other words, it should be understood that system (100) may be used to provide image guidance to the procedure described above where dilation catheter system (10) is used within the nasal cavity of a patient, with navigation guidewire (130) being substituted for guidewire (50). Various suitable components that may be used to form and drive field generators (122) will be apparent to those of ordinary skill in the art in view of the teachings herein.

IGS navigation system (100) of the present example further comprises a processor (110), which controls field generators (122) and other elements of IGS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 3 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. patent application Ser. No. 14/792,839, entitled "Guidewire Navigation for Sinuplasty," filed Jul. 7, 2015, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

A. Exemplary Navigation Guidewire

In the present example, navigational guidewire (130) includes one or more coils at the distal end of navigational guidewire (130). When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (100) to determine the location of the distal end of navigational guidewire (130) within a three dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three dimensional model of the anatomy within and adjacent to the patient's nasal cavity; in addition to being used to provide navigation for dilation catheter system (10) within the patient's nasal cavity. Alternatively, any other suitable device may be used to generate a three dimensional model of the anatomy within and adjacent to the patient's nasal cavity before navigational guidewire (130) is used to provide navigation for dilation catheter system (10) within the patient's nasal cavity. By way of example only, a model of this anatomy may be generated in accordance with at least some of the teachings of U.S. patent application Ser. No. 14/825,551, entitled "System and Method to Map Structures of Nasal Cavity," filed Aug. 13, 2015, the disclosure of which is incorporated by reference herein. Still other suitable ways in which a three dimensional model of the anatomy within and adjacent to the patient's nasal cavity may be generated will be apparent to those of ordinary skill in the art in view of the teachings herein. It should also be understood that, regardless of how or where the three dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

Figure 5:
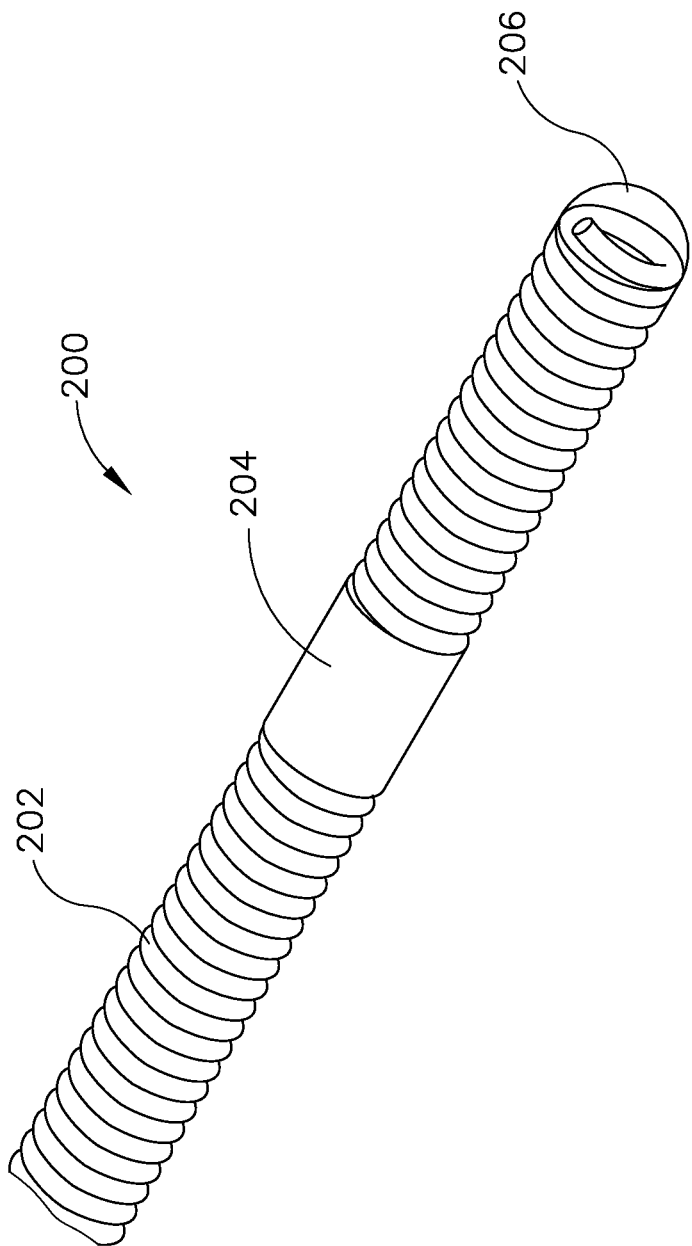
FIG. 5 depicts a perspective view of the distal end of an exemplary guidewire that may be incorporated into system dilation catheter of FIG. 1 and used with the navigation system of FIG. 3.
Figure 6:
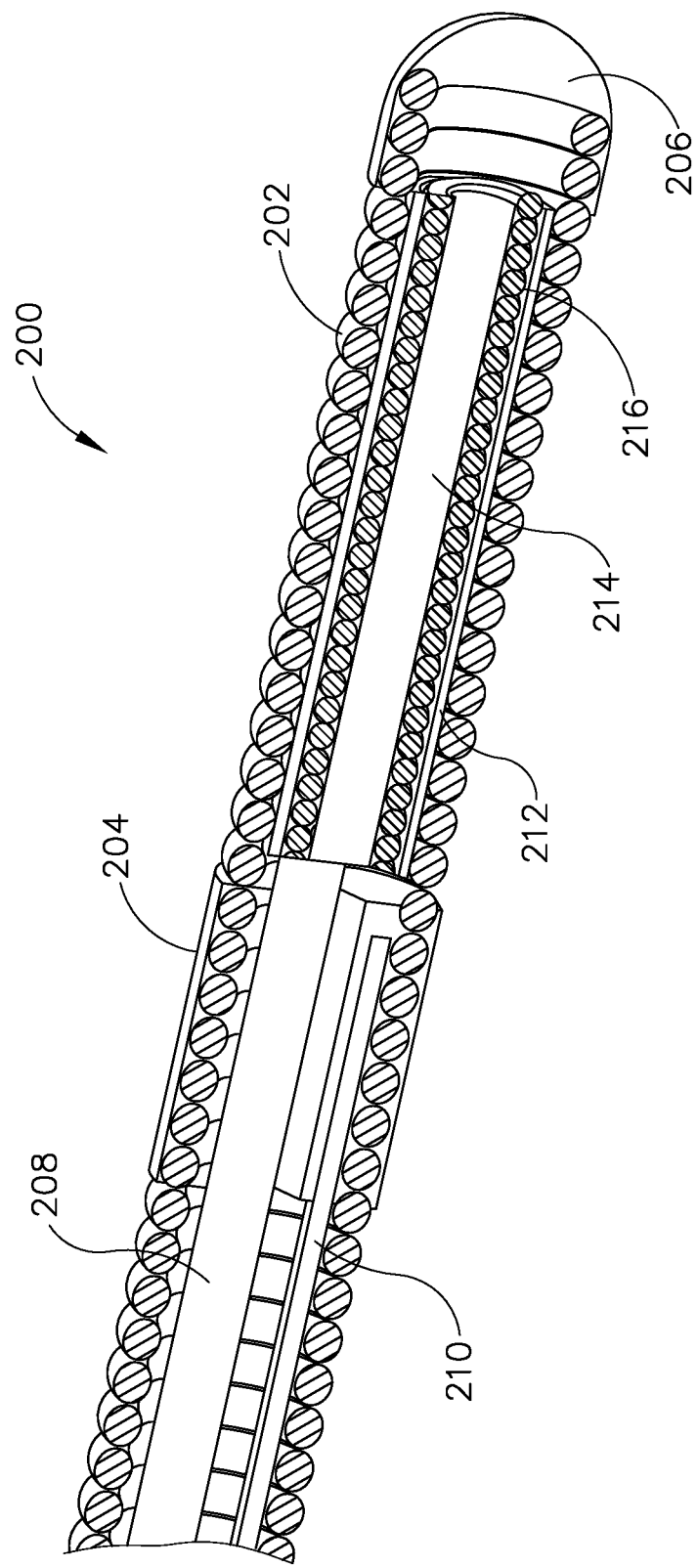
FIG. 6 depicts a perspective cross-sectional side view of the distal end of the guidewire of FIG. 5.

FIGS. 5-6 show an exemplary navigational guidewire (200) that may be used in place of navigational guidewire (130) described above. Navigational guidewire (200) of this example comprises an outer coil (202), a distal tip member (206), a core wire (210), a navigation coil (216), a navigation cable (208), and a solder joint (204). Outer coil (202) extends along the length of guidewire (200) and contains core wire (210), a proximal portion of navigation coil (216), and navigation cable (208). Outer coil (202) may be constructed in accordance with any suitable conventional guidewire outer coil.

Distal tip member (206) has an atraumatic dome shape and is secured to the distal end of outer coil (202). By way of example only, distal tip member (206) may be formed of an optically transmissive polymeric material and may be secured to the distal end of outer coil (202) using an interference fit, welding, adhesive, or using any other suitable techniques. As another merely illustrative example, distal tip member (206) may be formed by an optically transmissive adhesive that is applied to the distal end of outer coil (202) and then cured. It should also be understood that distal tip member (206) may be configured and operable like lens (58) described above.

In addition or in the alternative to being configured like lens (58), distal tip member (206) may comprise an electrically conductive material (e.g., gold or silver filled epoxy, etc.). As another merely illustrative example, distal tip member (206) may comprise a cap that is formed of an electrically conductive metal and/or some other electrically conductive material. Such a cap may be press-fit into the distal end of outer coil (202) and/or soldered to the distal end of outer coil (202). In versions where distal tip member (206) includes an electrically conductive material, the conductive material may be selected such that it has a relatively low magnetic permeability while having good electrical conductivity. Also in versions where distal tip member (206) includes an electrically conductive material, distal tip member may be in electrical continuity with outer coil (202), which may also be formed of an electrically conductive material. In the present example, outer coil (202) is grounded. Thus, the combination of an electrically conductive distal tip member (206) and outer coil (202) creates an electrical shield (e.g., similar to a Faraday cage), though it is transparent to the magnetic field. The combination may thus reduce electrical coupling to guidewire (200) such as capacitive/faradic coupling caused by the distal end of guidewire (200) coming into contact with the patient's body. Other suitable ways in which distal tip member (206) may be configured and operable will be apparent to those of ordinary skill in the art in view of the teachings herein.

In some versions, the distal end of an optical fiber (not shown) is optically coupled with distal tip member (206). The proximal end of the optical fiber is configured to couple with a light source. Various suitable ways in which an optical fiber may be coupled with a light source will be apparent to those of ordinary skill in the art in view of the teachings herein. The optical fiber is configured to provide a path for communication of light from the light source to distal tip member (206), such that distal tip member (206) can emit light generated by the light source. By way of example only one or more optical fibers may run alongside the outer diameter defined by navigation coil (216) in order to reach distal tip member (206). As another merely illustrative example, one or more optical fibers may terminate in the sidewall of outer coil (202) at a location just proximal to navigation coil (216), such that the one or more optical fibers may emit light through the sidewall of outer coil (202). In versions where guidewire (200) includes an optical fiber, it should be understood that any suitable number of optical fibers may be used. Various suitable ways in which guidewire (200) may incorporate one or more optical fibers will be apparent to those of ordinary skill in the art in view of the teachings herein. It should also be understood that guidewire (200) may simply lack any optical fibers.

Core wire (210) is configured to provide additional structural integrity to outer coil (202). In the present example, the proximal end of core wire (210) is fixedly secured to the proximal end of outer coil (202), while the distal end of core wire (210) is fixedly secured to the distal end of outer coil (202). Core wire (210) thus prevents or restricts longitudinal stretching of outer coil (202). Various suitable materials and configurations that may be used to form core wire (210) will be apparent to those of ordinary skill in the art in view of the teachings herein.

Navigation coil (216) is positioned within the distal end of outer coil (202). Navigation coil (216) thus presents an effective outer diameter that is less than the inner diameter defined by outer coil (202) in this example. In addition, the distal end of navigation coil (216) is positioned just proximal to the proximal face of tip member (206). In the present example, a core (214) of ferromagnetic material is positioned within the inner diameter that is defined by navigation coil (216). Core (214) extends along the full length of navigation coil (216) in this example. By way of example only, core (214) may be formed of iron or some other ferromagnetic material. Navigation coil (216) is configured to cooperate with IGS navigation system (100) to provide signals indicative of the positioning of the distal end of guidewire (200) within the patient, as described above. Navigation cable (208) is coupled with the proximal end of navigation coil (216) and transmits the signals from navigation coil (216) to IGS navigation system (100). It should therefore be understood that the proximal end of guidewire (200) may include feature that is configured to couple with coupling unit (132). A merely illustrative example of such a coupling feature is described in greater detail below.

A support tube (212) is positioned about navigation coil (216) in the present example. Support tube (212) of the present example has a cylindraceous configuration. Support tube (212) thus presents an outer diameter that is less than the inner diameter defined by outer coil (202). Support tube (212) extends along the full length of navigation coil (216), such that the distal and proximal ends of support tube (212) are flush with the distal end proximal ends of navigation coil (216). Alternatively, support tube (212) may have any other suitable length and/or positioning in relation to the length and/or positioning of navigation coil (216). In the present example, the outer surface of support tube (212) is adhered to the inner surface of outer coil (202) by an adhesive; and the inner surface of support tube (212) is adhered to the outer surface of navigation coil (216) by adhesive. Alternatively, any other suitable methods may be used to secure support tube (212) to outer coil (202) and/or navigation coil (216).

It should also be understood that support tube (212) may alternatively be secured to just one coil (202, 216) without also being secured to the other coil (202, 216).

Support tube (212) of the present example provides further structural integrity to navigation coil (216), reducing the likelihood that navigation coil (216) will be damaged as tip member (206) bumps into anatomical structures within the patient and other structures during use of guidewire (200). Support tube (212) of the present example is also configured to not have an adverse impact on the signal provided by navigation coil (216). In some versions, support tube (212) is constructed of a non-conductive polymeric material such as polyamide. Other suitable ways in which support tube (212) may be configured will be apparent to those of ordinary skill in the art in view of the teachings herein.

Solder joint (204) is used to secure at least some of the above-described components together. In the present example, solder joint (204) is proximal to tip member (206) and extends about outer coil (202), core wire (210), and navigation cable (208). Navigation coil (216) proximally terminates distal to the longitudinal position of solder joint (204). In addition to securing components of guidewire (200) together, solder joint (204) may also provide some degree of structural integrity to guidewire (200). It should be understood that solder joint (204) is merely optional such that components of guidewire (200) may be secured together in any other suitable fashion.

By way of example only, outer coil (202) may have an effective outer diameter of approximately 0.035 inches and an inner diameter of approximately 0.022 inches. Outer coil (202) may also be formed by a 316 stainless steel (or nitinol) wire having a thickness of approximately 0.006 inches, with a round cross-sectional profile. Navigation coil (216) may have a length of approximately 0.118 inches and an effective outer diameter of approximately 0.022 inches. Core (214) may have an outer diameter of approximately 0.010 inches. Of course, all of these dimensions are just merely illustrative examples. Other suitable dimensions will be apparent to those of ordinary skill in the art in view of the teachings herein.

Figure 7:
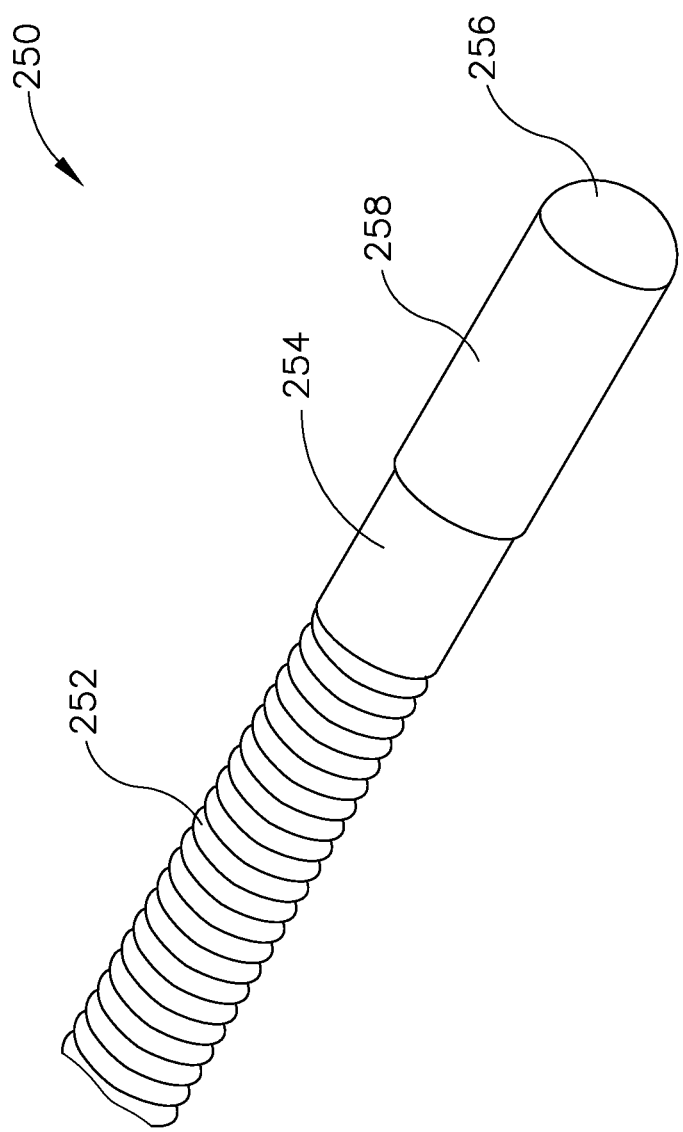
FIG. 7 depicts a perspective view of the distal end of another exemplary guidewire that may be incorporated into system dilation catheter of FIG. 1 and used with the navigation system of FIG. 3.
Figure 8:
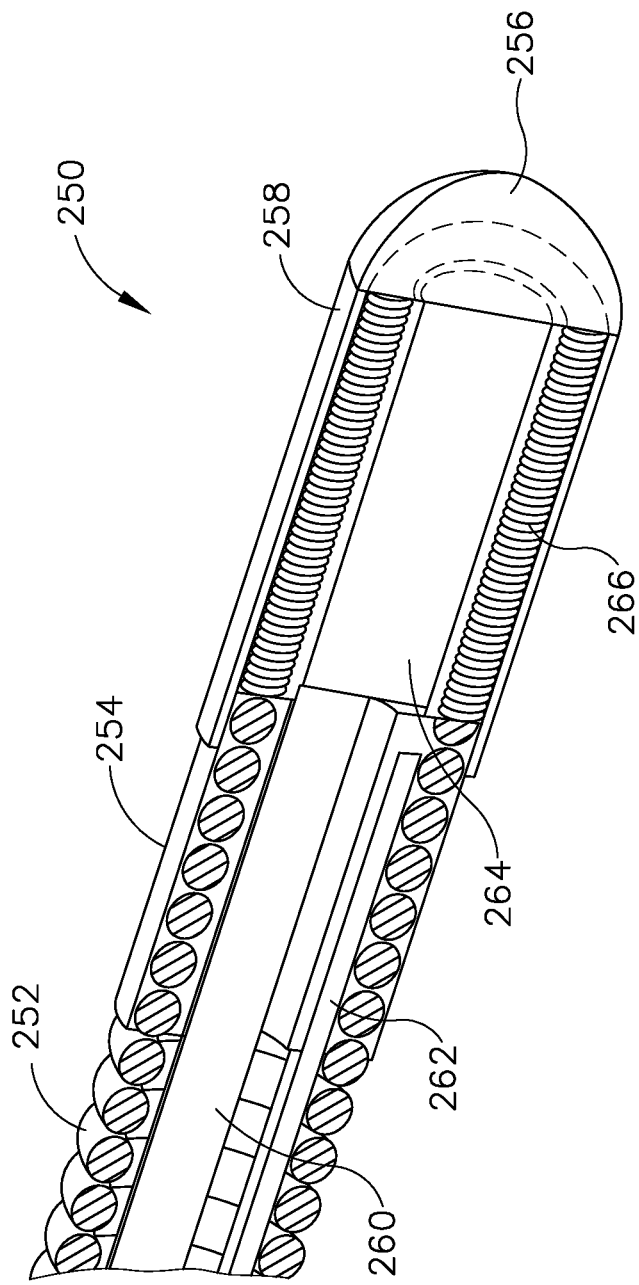
FIG. 8 depicts a perspective cross-sectional side view of the distal end of the guidewire of FIG. 7.

FIGS. 7-8 show another exemplary navigational guidewire (250) that may be used in place of navigational guidewire (130) described above. Navigational guidewire (250) of this example comprises an outer coil (252), a distal tip member (256), a core wire (262), a navigation coil (266), a navigation cable (260), a solder joint (254), and an outer tube (258) surrounding navigation coil (266). Outer coil (252) extends along a substantial portion of the length of guidewire (200) and contains core wire (262) and navigation cable (260). Outer coil (252) may be constructed in accordance with any suitable conventional guidewire outer coil. Unlike other examples described herein, outer coil (252) distally terminates at solder joint (254), which is located the proximal end of navigation coil (266) and at the proximal end of outer tube (258). In some versions, outer coil (252) is formed by a round wire that is wrapped in a helical configuration. In some other versions, outer coil (252) is formed by a flat wire that is wrapped in a helical configuration. Other suitable ways in which outer coil (252) may be formed will be apparent to those of ordinary skill in the art in view of the teachings herein.

Distal tip member (256) has an atraumatic dome shape and is secured to the distal end of outer tube (258), at the distal end of navigation coil (266). By way of example only, distal tip member (256) may be formed of an optically transmissive polymeric material and may be secured to the distal end of outer tube (258) using an interference fit, welding, adhesive, or using any other suitable techniques. As another merely illustrative example, distal tip member (256) may be formed by an optically transmissive adhesive that is applied to the distal end of outer tube (258) and then cured. It should also be understood that distal tip member (256) may be configured and operable like lens (58) described above. In some variations, however, distal tip member (256) is not optically transmissive at all. Other suitable ways in which distal tip member (256) may be configured and operable will be apparent to those of ordinary skill in the art in view of the teachings herein.

In some versions (e.g., versions where distal tip member (256) is optically transmissive), the distal end of an optical fiber (not shown) is optically coupled with distal tip member (256). The proximal end of the optical fiber is configured to couple with a light source. Various suitable ways in which an optical fiber may be coupled with a light source will be apparent to those of ordinary skill in the art in view of the teachings herein. The optical fiber is configured to provide a path for communication of light from the light source to distal tip member (256), such that distal tip member (256) can emit light generated by the light source. By way of example only one or more optical fibers may run alongside the outer diameter defined by navigation coil (266) in order to reach distal tip member (256). As another merely illustrative example, one or more optical fibers may terminate in the sidewall of outer coil (252) at a location just proximal outer tube (258), such that the one or more optical fibers may emit light through the sidewall of outer tube (258). In versions where guidewire (250) includes an optical fiber, it should be understood that any suitable number of optical fibers may be used. Various suitable ways in which guidewire (250) may incorporate one or more optical fibers will be apparent to those of ordinary skill in the art in view of the teachings herein. It should also be understood that guidewire (250) may simply lack any optical fibers.

Core wire (262) is configured to provide additional structural integrity to outer coil (252). In the present example, the proximal end of core wire (262) is fixedly secured to the proximal end of outer coil (252), while the distal end of core wire (262) is fixedly secured to the distal end of outer coil (252). Core wire (262) thus prevents or restricts longitudinal stretching of outer coil (252). Various suitable materials and configurations that may be used to form core wire (262) will be apparent to those of ordinary skill in the art in view of the teachings herein.

Navigation coil (266) is positioned distal the distal end of outer coil (252) and within outer tube (258), such that coils (252, 266) are in a longitudinally stacked relationship. In the present example, navigation coil (266) presents an effective outer diameter that is greater than the inner diameter defined by outer coil (252) in this example. In some versions, the configuration of guidewire (250) allows navigation coil (266) to have an effective outer diameter that is larger than the effective outer diameter of navigation coils in other guidewires described herein. This may provide navigation coil (266) with a greater sensitivity to fields generated by IGS navigation system (100), thereby making guidewire (250) more useful in navigation than other guidewires described herein. In addition or in the alternative, the configuration of guidewire (250) allows outer coil (252) to have an effective outer diameter that is smaller than the effective outer diameter of outer coils in other guidewires described herein. It should also be understood that the configuration of guidewire (250) allows navigation coil (266) to have an effective length that is shorter than the effective length of navigation coils in other guidewires described herein. This reduction in effective length may effectively reduce the length of the relatively stiff section at the distal end of guidewire (250), as compared to other guidewire construction described herein. By having a shorter stiff section at the distal end of guidewire (250), guidewire (250) may be capable of accessing a greater variety of anatomical structures.

The distal end of navigation coil (266) is positioned just proximal to the proximal face of tip member (256). In the present example, a core (264) of ferromagnetic material is positioned within the inner diameter that is defined by navigation coil (266). Core (264) extends along the full length of navigation coil (266) in this example. By way of example only, core (264) may be formed of iron or some other ferromagnetic material. Navigation coil (266) is configured to cooperate with IGS navigation system (100) to provide signals indicative of the positioning of the distal end of guidewire (250) within the patient, as described above. Navigation cable (260) is coupled with the proximal end of navigation coil (266) and transmits the signals from navigation coil (266) to IGS navigation system (100). It should therefore be understood that the proximal end of guidewire (250) may include feature that is configured to couple with coupling unit (132). A merely illustrative example of such a coupling feature is described in greater detail below.

As noted above, outer tube (258) is positioned about navigation coil (266) in the present example and extends from the distal end of outer coil (252) to the proximal end of tip member (256). Outer tube (258) of the present example has a cylindraceous configuration. Outer tube (258) presents an inner diameter that is larger than the outer diameter defined by outer coil (252), such that the distal end of outer coil (252) fits within the proximal end of outer tube (258). Outer tube (258) extends beyond the full length of navigation coil (266). In the present example, navigation coil (266) is adhered to the inner surface of outer tube (258) by an adhesive. Outer tube (258) is also secured to outer coil (252) and/or solder joint (254) by an adhesive. As another merely illustrative example, outer tube (258) may be secured to the distal end of outer coil (252) through a lap joint. Alternatively, any other suitable methods may be used to secure outer tube (258) to outer coil (252) and/or navigation coil (266).

Outer tube (258) of the present example provides further structural integrity to navigation coil (266), reducing the likelihood that navigation coil (266) will be damaged as tip member (256) bumps into anatomical structures within the patient and other structures during use of guidewire (250). Outer tube (258) of the present example is also configured to not have an adverse impact on the signal provided by navigation coil (266). In some versions, outer tube (258) is constructed of a non-conductive polymeric material such as polyamide. In some other versions, outer tube (258) is constructed of titanium, nitinol, 316 stainless steel, and/or some other material(s). Other suitable ways in which outer tube (258) may be configured will be apparent to those of ordinary skill in the art in view of the teachings herein.

Solder joint (254) is used to secure at least some of the above-described components together. In the present example, solder joint (254) is proximal to navigation coil (266) and extends about outer coil (252), core wire (262), and navigation cable (260). Navigation coil (266) proximally terminates distal to the longitudinal position of solder joint (254). In addition to securing components of guidewire (250) together, solder joint (254) may also provide some degree of structural integrity to guidewire (250). It should be understood that solder joint (254) is merely optional such that components of guidewire (250) may be secured together in any other suitable fashion.

By way of example only, outer coil (252) may have an effective outer diameter of approximately 0.0315 inches and an inner diameter of approximately 0.0210 inches. Outer coil (252) may also be formed by a 316 stainless steel (or nitinol) wire having a flat cross-sectional profile that is approximately 0.005 inches by approximately 0.007 inches. Navigation coil (266) may have a length of approximately 0.059 inches and an effective outer diameter of approximately 0.031 inches. Core (264) may have an outer diameter of approximately 0.015 inches. Outer tube (258) may have an outer diameter of approximately 0.036 inches. Of course, all of these dimensions are just merely illustrative examples. Other suitable dimensions will be apparent to those of ordinary skill in the art in view of the teachings herein.

Still further merely illustrative examples of navigational guidewires are disclosed in U.S. patent application Ser. No. 14/835,108, entitled "Guidewire with Navigation Sensor," filed Aug. 25, 2015, the disclosure of which is incorporated by reference herein. It should also be understood that various other kinds of instruments may incorporate one or more sensor coils like the various navigational guidewires (130, 200, 250) described herein. Such instruments may thus be tracked by IGS navigation system (100) in accordance with the teachings herein.

B. Exemplary Registration and Calibration of Image Guided Surgery Navigation System Referring back to the components shown in FIGS. 3-4, prior to being placed on the patient, field generators (122) in frame (120) may be calibrated by positioning a calibration coil (not shown) in the vicinity of field generators (122) in known locations and orientations relative to frame (120). In some instances, the same navigational guidewire (130) that will be used in the surgical procedure is also used to perform calibration, such that a coil in navigational guidewire (130) serves as the calibration coil. Signals are induced in the calibration coil by the alternating magnetic fields generated by field generators (122), and processor (110) acquires and records the signals. Processor (110) then formulates a calibration relationship between (i) the locations and orientations of the calibration coil and (ii) the recorded signals for these locations and orientations of the calibration coil.

Once the calibration relationship has been formulated, frame (120) may be placed on the head of the patient. Alternatively, as noted above and as will be described in greater detail below, some versions may provide field generators (122) on structures other than frame (120). In the present example, however, after frame (120) has been placed on the head of the patient, frame (120) is fixed in position and registered with external features of the head of the patient, for example by imaging the head of the patient with the attached frame (120) from a number of different angles. The frame (120) registration also registers field generators (122) with the external features of the patient. Alternatively or additionally, the registration may include placing the calibration coil in one or more known locations and orientations with respect to the external features of the patient as well as with frame (120).

In addition to registering with the external features of the patient, the registration of the present example further includes registration with an image of the sinuses of the patient. In some instances, this image of the sinuses of the patient has been acquired prior to a projected sinuplasty procedure. The preexisting image of the sinuses of the patient may comprise a CT (computerized tomography)

image, an MRI (magnetic resonance imaging) image, an ultrasound image, a combination of such images, and/or one or more images captured using any other suitable imaging modality. It should be understood that, regardless of how the image of the sinuses of the patient has been acquired, frame (120) is in registration with both the sinuses of the patient and the external features of the patient in the present example.

III. EXEMPLARY ALTERNATIVE FIELD GENERATING STRUCTURES

Figure 9:
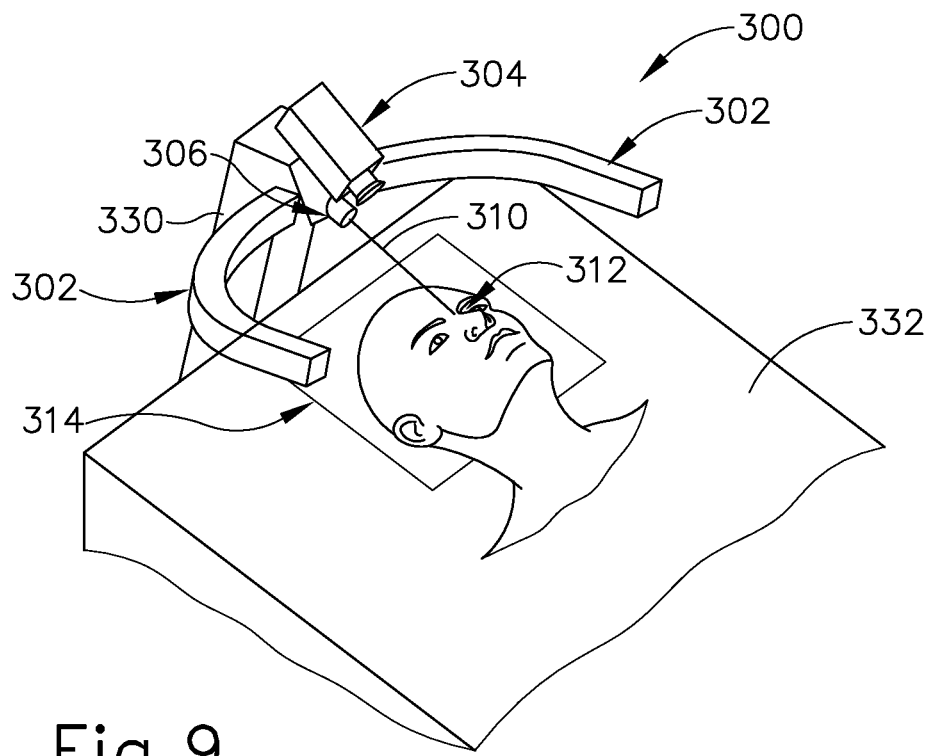
FIG. 9 depicts a schematic view of a patient positioned in relation to components of another exemplary sinus surgery navigation system during a registration process.
Figure 10:
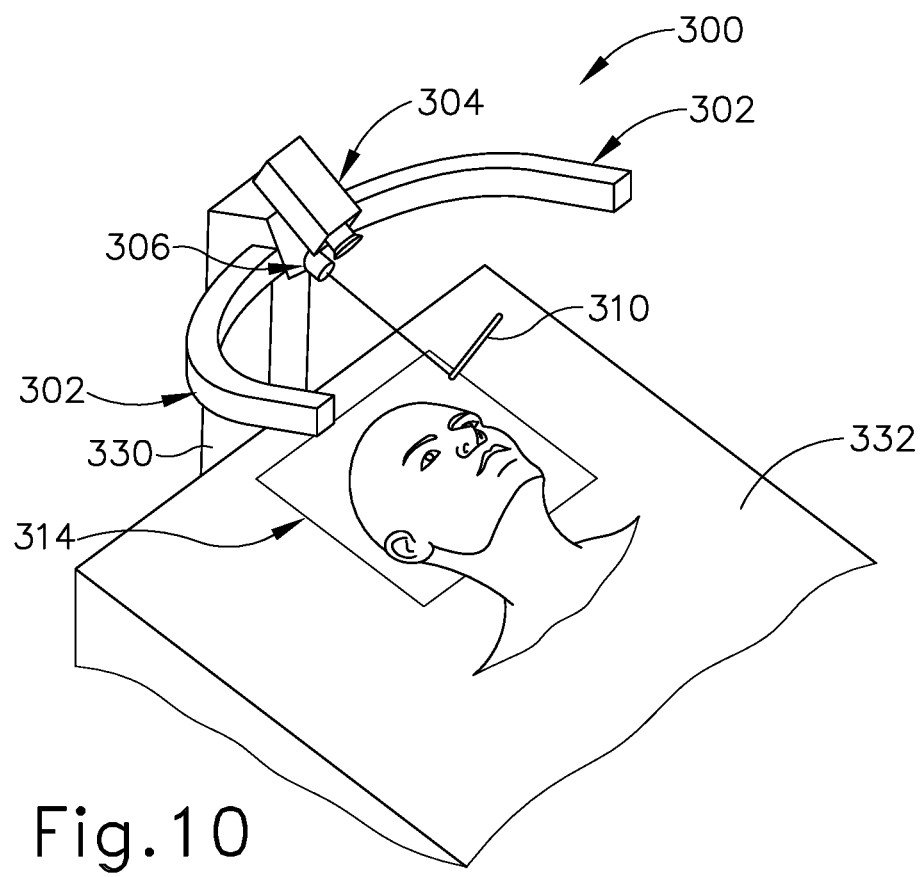
FIG. 10 depicts a schematic view of a patient positioned in relation to the navigation system components of FIG. 9 during an instrument tracking process.

As noted above, field generators (122) need not necessarily be mounted directly to the patient's head via frame (120) or some other structure. By way of example only, FIGS. 9-10 show an exemplary alternative assembly (300) that may be used to house field generators (122). Assembly (300) of this example comprises a set of arms (302) mounted to a post (330). Post (330) is mounted to a table (332) upon which the patient is supported. Arms (302) extend outwardly over the head of the patient and together form an arc. In some versions, this arc extends along an angular range of approximately 180°. Alternatively, arms (302) may together define an arc that extends along an angular range that is more or less than approximately 180°. While not shown in FIGS. 9-10, it should be understood that field generators (122) are housed within arms (302). Alternatively, field generators (122) may be mounted externally to arms (302).

Assembly (300) of the present example further comprises a camera (304). Camera (304) is operable to capture video images of the patient's head. Various suitable forms that camera (304) may take will be apparent to those of ordinary skill in the art in view of the teachings herein. In the present example, camera (304) provides a sufficient field of view such that the entire head of the patient is captured in the video image. Camera (304) is thus fixably mounted on post (330). In some other versions, camera (304) is movably mounted on post (330) such that the position and/or orientation of camera (304) may be adjusted. Camera (304) is coupled with processor (110) of IGS navigation system (100). Processor (110) is thus operable to process video image data from camera (304) and drive display unit (114) to display video images from camera (304). For instance, processor (110) may drive display unit (114) to display a superimposed video image from camera (304) on a preexisting CT image of the same patient. Processor (110) may further execute algorithms to adjust the positioning and zoom level of the video image to provide a best fit for the CT image. Other suitable ways in which processor (110) may use video image data from camera (304) will be apparent to those of ordinary skill in the art in view of the teachings herein.

Assembly (300) of the present example further comprises a laser source (306). Laser source (306) is operable to project a laser beam (310) onto the patient's head within an approximate working area (314). In some instances as will be described in greater detail below with reference to FIG. 10, laser source (306) is also operable to project a laser beam (310) onto an instrument (320) that is located near the patient's head. In some versions, laser source (306) is mounted to post (330) via a movable fixture that is motorized (e.g. via servo motor), such that laser source (306) may be controllably and automatically moved to re-orient laser beam (310). In addition or in the alternative, laser source (306) may include one or more movable features (e.g., mirrors, collimators, etc.) that are configured to controllably and automatically re-orient and/or otherwise reconfigure laser beam (310). It should also be understood that laser source (306) may be configured to project a plurality of laser beams (310). In addition or in the alternative, laser source (306) may actually comprise a plurality of laser sources. Various suitable components that may be used to form laser source (306) will be apparent to those of ordinary skill in the art in view of the teachings herein. Laser source (306) is coupled with processor (110) of IGS navigation system (100). Processor (110) is thus operable to drive laser source (306) and any movable components associated with laser source (306).

Figure 11:
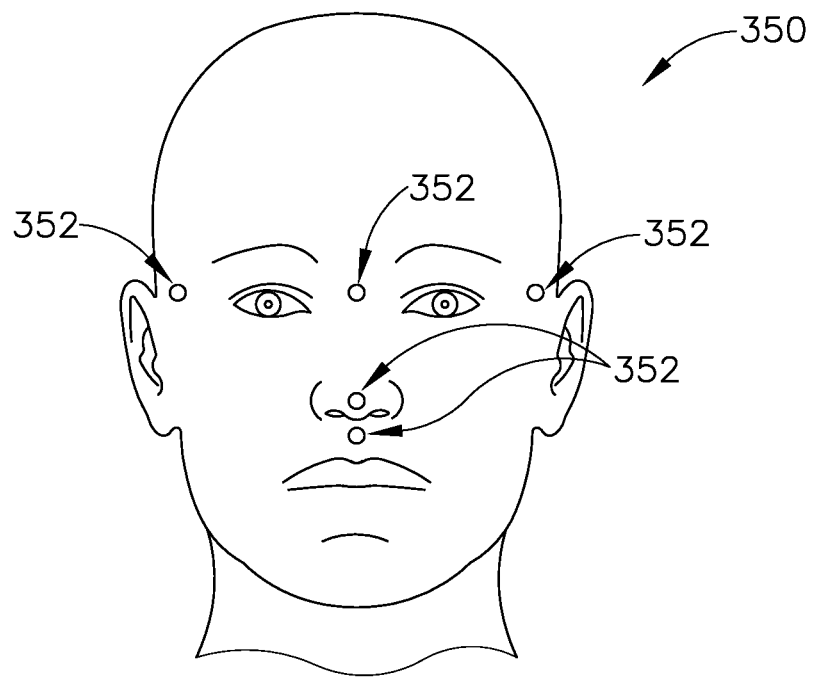
FIG. 11 depicts an exemplary video feed view of the patient of FIG. 9 during the registration process of FIG. 9.
Figure 12:
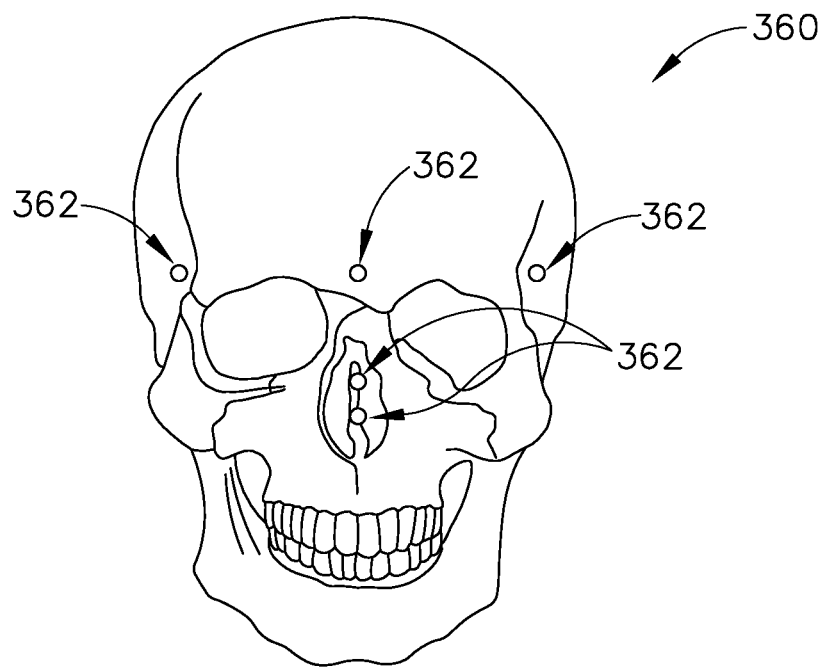
FIG. 12 depicts an exemplary CAT scan view of the patient of FIG. 9 during the registration process of FIG. 9.

As shown in FIG. 9, laser beam (310) provides a registration point (312) on the patient's head within approximate working area (314). Camera (304) may simultaneously capture video image data of the patient's head within approximate working area (314). Processor (110) may drive display unit (114) to render the video image (350) shown in FIG. 11. As shown, video image (350) shows the patient's head with a plurality of registration points (352) thereon. In some versions, laser source (306) projects all registration points (352) simultaneously. In some other versions, laser source (306) projects registration points (352) individually, in a succession. Processor (110) may also drive display unit (114) to render the CT image (360) shown in FIG. 12. In some versions, images (350, 360) are displayed separately from each other on display unit (114) (e.g., on the same screen simultaneously on separate panels or windows). In some other versions, images (350, 360) are blended through superimposition to form a composite image. In the event that image (360) is shown separately, image (360) may also include registration points (362) corresponding to the location of registration points (352).

With registration point (312) or registration points (352) projected, the operator may manipulate an instrument such as navigational guidewire (130, 200, 250) to bring the calibration coil (i.e., navigation coil (216, 266)) into proximity of registration point (312) or registration points (352). In particular, the operator may touch the distal tip of navigational guidewire (130, 200, 250) against the patient's face at the location of registration point (312) or registration points (352). At each registration point (312, 352), the operator may interact with operating controls (112) to indicate the presence of the distal tip of navigational guidewire (130, 200, 250) at each registration point (312, 352). In response to this input, processor (110) may log the data provided by the calibration coil (i.e., navigation coil (216, 266)) in response to the field generated by field generators (122) to determine the location of the calibration coil within 3-dimensional space. Processor (110) may further correlate this position information with the real time video image captured by camera (304); and also with the CT image (360).

Once the operator has completed the above process with respect to each and every registration point (312, 352), processor (110) may have an accurate sense of where the patient's anatomical structures are located based on the combination of CT image (360), video image (350), and data captured from the calibration coil during the registration process. In other words, processor (110) may be able to correlate the 3-dimensional space captured in the CT image (360) with the 3-dimensional space captured within the video image (350); and also correlate the real-time position of the distal tip of navigational guidewire (130, 200, 250) within such 3-dimensional space. In the event that the patient's head moves after the registration and calibration process is complete, processor (110) may monitor such movement through video image (350) and make real-time corrections to the spatial correlations. While five registration points (352, 362) are used in the example shown in FIGS. 11-12, it should be understood that any other suitable number of registration points (352, 362) may be used to provide a suitable correlation between the 3-dimensional space captured in the CT image (360) and the actual 3-dimensional space in which the patient and navigational guidewire (130, 200, 250) are currently situated. In addition, while the foregoing example describes a navigational guidewire (130, 200, 250) being used as part of this process, it should be understood that any other suitable instrument having a coil (or other sensor) may be used to perform this registration and calibration process.

Figure 13:
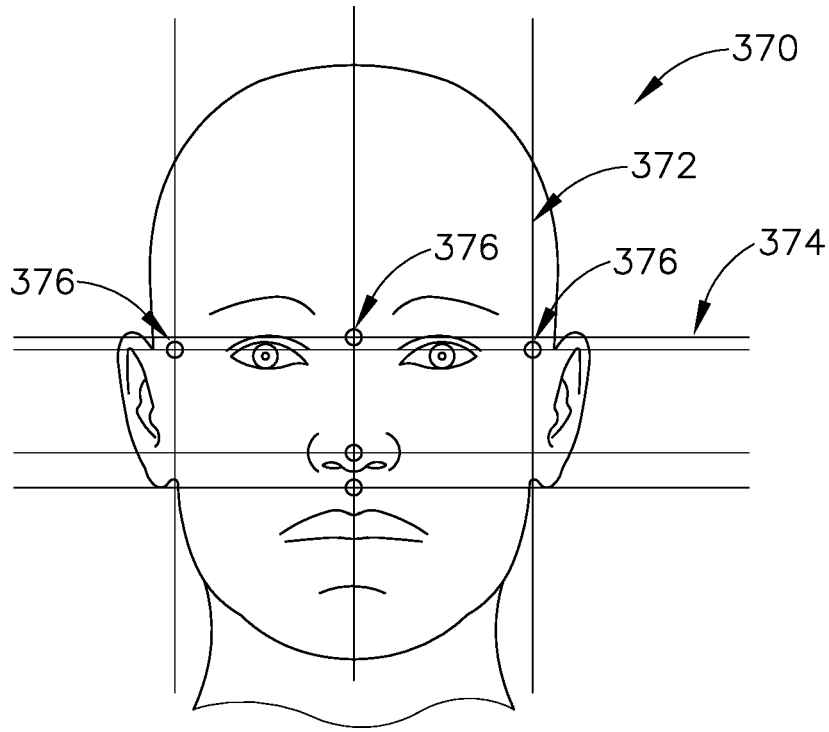
FIG. 13 depicts another exemplary video feed view of the patient of FIG. 9 during the registration process of FIG. 9.
Figure 14:
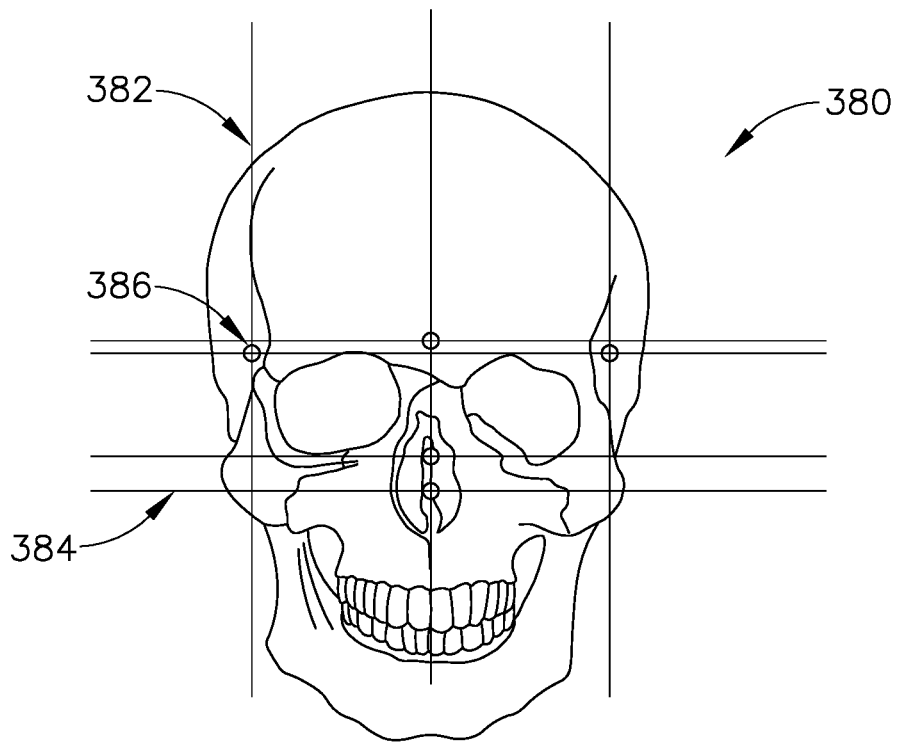
FIG. 14 depicts another exemplary CAT scan view of the patient of FIG. 9 during the registration process of FIG. 9.
Figure 15:
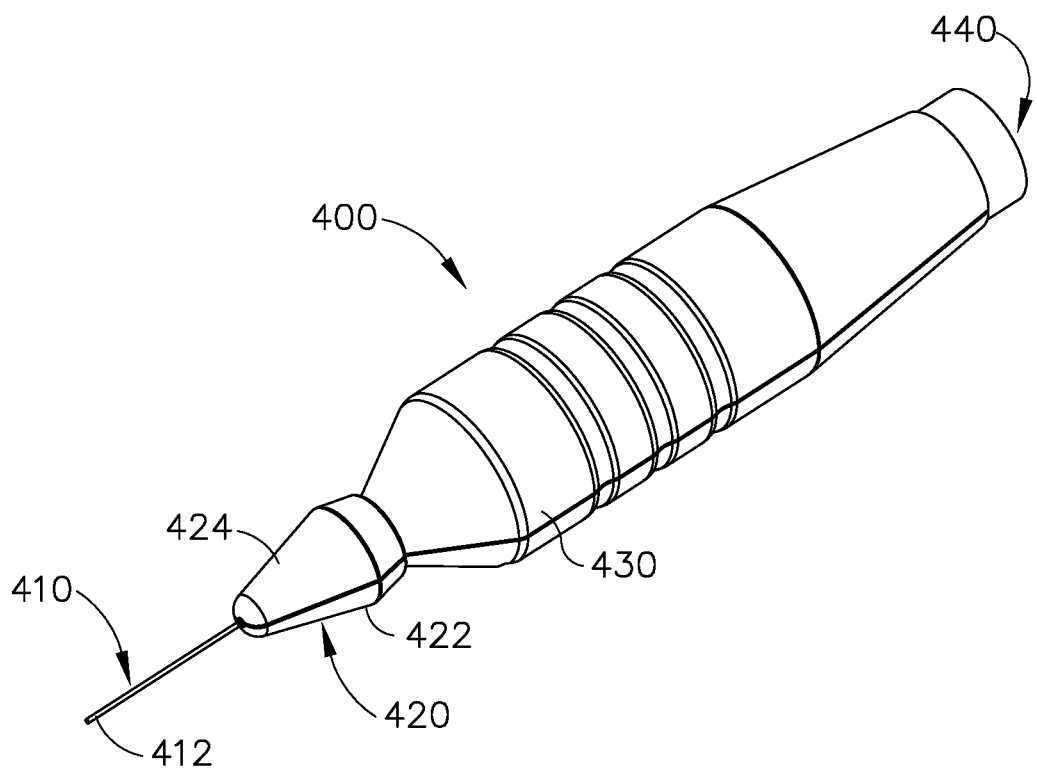
FIG. 15 depicts a perspective view of an exemplary coupling assembly located at the proximal end of a navigational guidewire.

As one merely illustrative variation, laser source (306) may project a grid on the patient's head. This grid may appear in the video image (370) that is rendered through display screen (114) as shown in FIG. 13. In this example, the grid includes vertical lines (372) and horizontal lines (374) that intersect at registration points (376). The grid in video image (370) may thus facilitate operator identification of registration points (376). Similarly, processor (110) may provide a grid formed by vertical lines (382) and horizontal lines (384) that intersect at registration points (386) in the CT image (380) that is rendered through display screen (114) as shown in FIG. 14. In addition to facilitating operator identification of registration points (376), the grids may facilitate processor (110) correlation between the 3-dimensional space captured in the CT image (380) and the actual 3-dimensional space in which the patient and navigational guidewire (130, 200, 250) are currently situated.

In addition to providing registration points (312, 352, 376) on the patient's head, laser source (306) may be used to provide real-time tracking of an instrument (320) as shown in FIG. 10. By way of example only, instrument (320) may comprise navigational guidewire (130, 200, 250) or any other suitable instrument having a coil (or other sensor). In this example, laser beam (310) projects to the distal tip of instrument (320) and follows the distal tip of instrument (320) as instrument (320) moves within 3-dimensional space. By way of example only, such tracking may be performed using a solid state laser and galvanometer mirror. This real-time tracking laser beam (310) may provide the operator with active visual feedback regarding the location of instrument (320) within the 3-dimensional space. In addition, laser beam (310) may indicate to the operator where to touch or otherwise register instrument (320) on the patient's anatomy. Processor (110) may monitor this via video camera (304) and provide a visual and software affirmation as to how close the operator has placed instrument (320) in relation to a registration point on the patient's anatomy.

As yet another merely illustrative example, when instrument (320) is inserted into the patient's head (e.g., via the nose, via the mouth, via the ear, etc.), such that the distal tip is located within the patient's head (e.g., within the nasal cavity, etc.), laser beam (310) may continue to project onto the patient's head. In particular, laser beam (310) may project a spot onto the patient's head in the external location corresponding to the internal location of the distal tip of instrument (320). For instance, if the distal tip of instrument (320) is within a frontal sinus, laser beam (310) may project a spot onto the patient's forehead at the position associated with the instrument (320) location in the frontal sinus. As another example, if the distal tip of instrument (320) is within a maxillary sinus, laser beam (310) may project a spot onto the patient's cheek at the position associated with the instrument (320) location in the maxillary sinus. As instrument (320) continues to move within the patient's head, laser beam (310) may correspondingly move in real time to continue such tracking.

In some versions, processor (110) will vary the color of registration points (352, 362, 376, 386) as rendered on display screen (114), based on the perceived accuracy of the registration. For instance, a registration point (352, 362, 376, 386) may be colored red to indicate a low level of accuracy; yellow to indicate a moderate level of accuracy; or green to indicate a high level of accuracy. Other suitable ways in which processor (110) may indicate the accuracy of registration to an operator will be apparent to those of ordinary skill in the art in view of the teachings herein.

While the foregoing example provides the use of both a video camera (304) and a laser source (306) to assist in the registration and calibration process, it should be understood that some alternative versions may just use video camera (304) without using a laser source (306). Similarly, some alternative versions may just use laser source (306) without using a video camera (304) in the registration and calibration process.

IV. EXEMPLARY ROTARY COUPLING ASSEMBLY FOR NAVIGATIONAL GUIDEWIRE

When an operator uses a navigational guidewire (130, 200, 250) in a surgical procedure, the operator may tend to rotate navigational guidewire (130, 200, 250) about the longitudinal axis of navigational guidewire (130, 200, 250). Such rotations may be more or less than 360° about the longitudinal axis of navigational guidewire (130, 200, 250). Such rotations may pose concerns at the proximal end of navigational guidewire (130, 200, 250). In particular, a navigation cable (208, 260) within navigational guidewire (130, 200, 250) may need to electrically couple with one or more corresponding components in coupling unit (132) in order to provide a communication path from navigation coil (216, 266) to processor (110). If navigation cable (208, 260) is fixedly coupled with coupling unit (132), rotation of navigational guidewire (130, 200, 250) may place stress on the fixed coupling, which may present a risk of failure at the fixed coupling. It may therefore be desirable to provide a coupling between navigation cable (208, 260) and coupling unit (132) that provides at least some degree of play or relative movement between navigation cable (208, 260) and coupling unit (132) to accommodate rotation of navigational guidewire (130, 200, 250) during normal use of navigational guidewire (130, 200, 250) in a surgical procedure, reducing or eliminating the risks of failure that may otherwise be associated with a fixed coupling.

Figure 16:
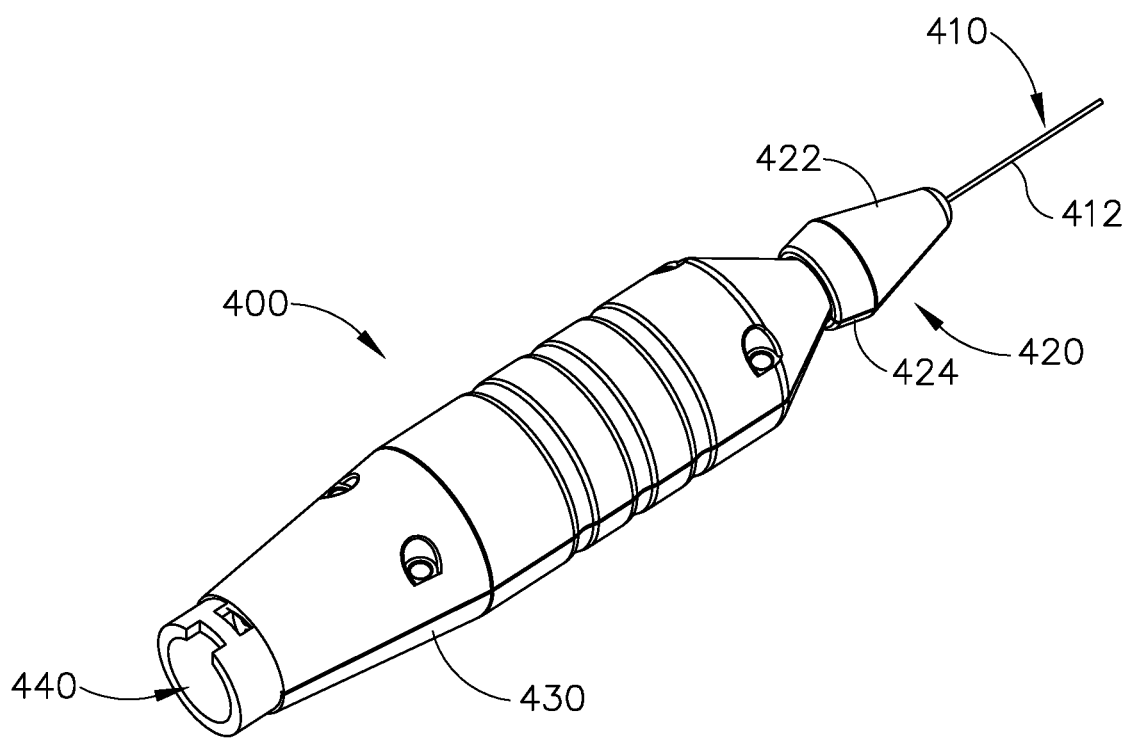
FIG. 16 depicts another perspective view of the coupling assembly and navigational guidewire of FIG. 15.
Figure 17:
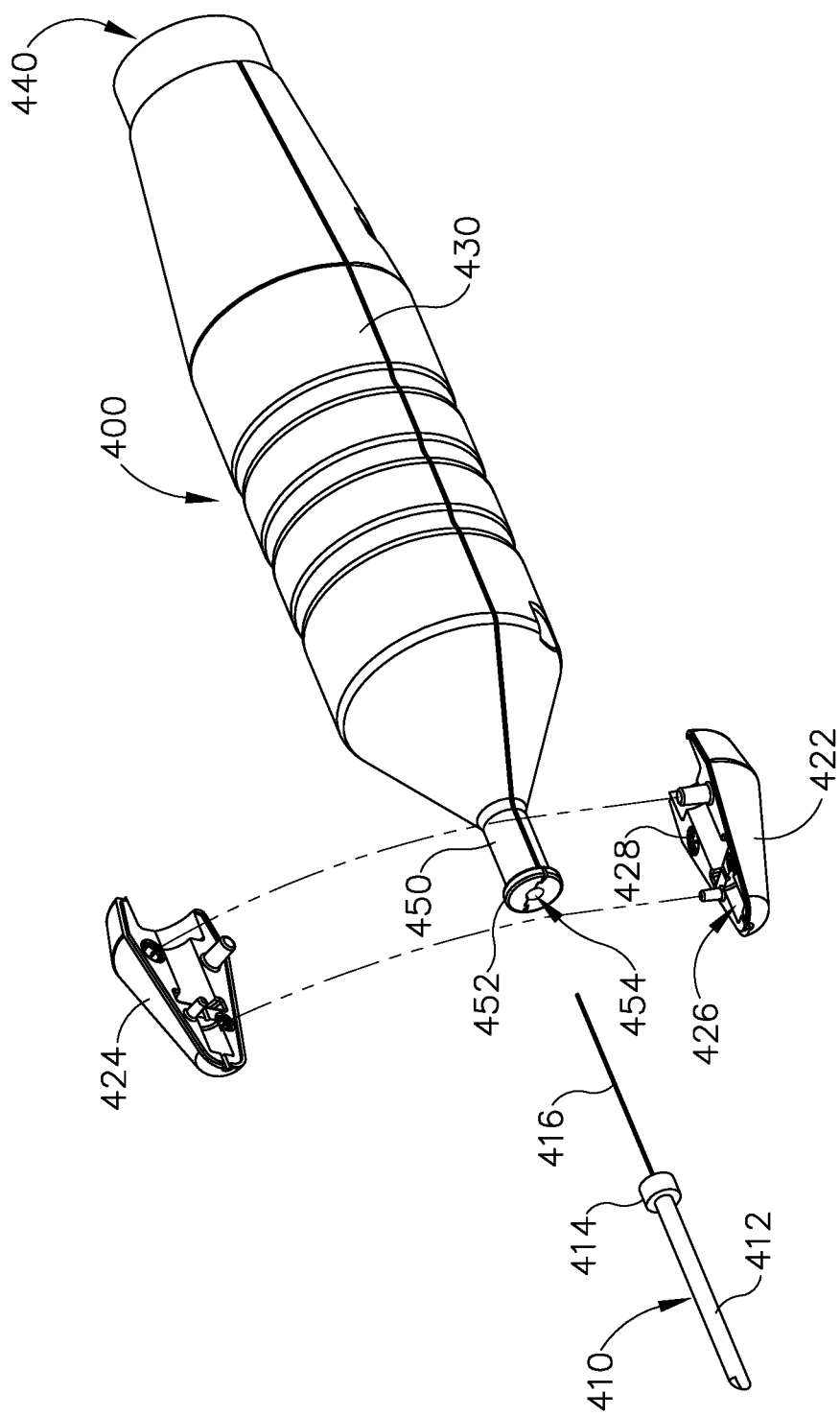
FIG. 17 depicts a partially exploded view of the coupling assembly and navigational guidewire of FIG. 15.

FIGS. 15-18 show an exemplary coupling assembly (400) that secured to the proximal end of a navigational guidewire (410). It should be understood that navigational guidewire (410) of this example may be constructed and operable just like any of the navigational guidewires (130, 200, 250) described above. In particular, as best seen in FIG. 17, navigational guidewire (410) comprises an outer coil (412) and a navigation cable (416). Outer coil (412) may be configured and operable just like outer coils (202, 252) described above. Navigation cable (416) may be constructed and operable just like navigation cables (208, 260) described above. It should therefore be understood that the distal end of navigational guidewire (410) may further include a coil like navigation coil (216, 266) described above; and that this coil may be coupled with navigation cable (416). Navigational guidewire (410) of thus example further includes a cylindraceous anchor (414) that is fixedly secured to the proximal end of outer coil (412). In versions where navigational guidewire (410) includes a core wire (e.g., like core wires (210, 262) described above), the proximal end of the core wire may also be fixedly secured to anchor (414). Navigation cable (416) extends proximally from anchor (414).

Figure 18:
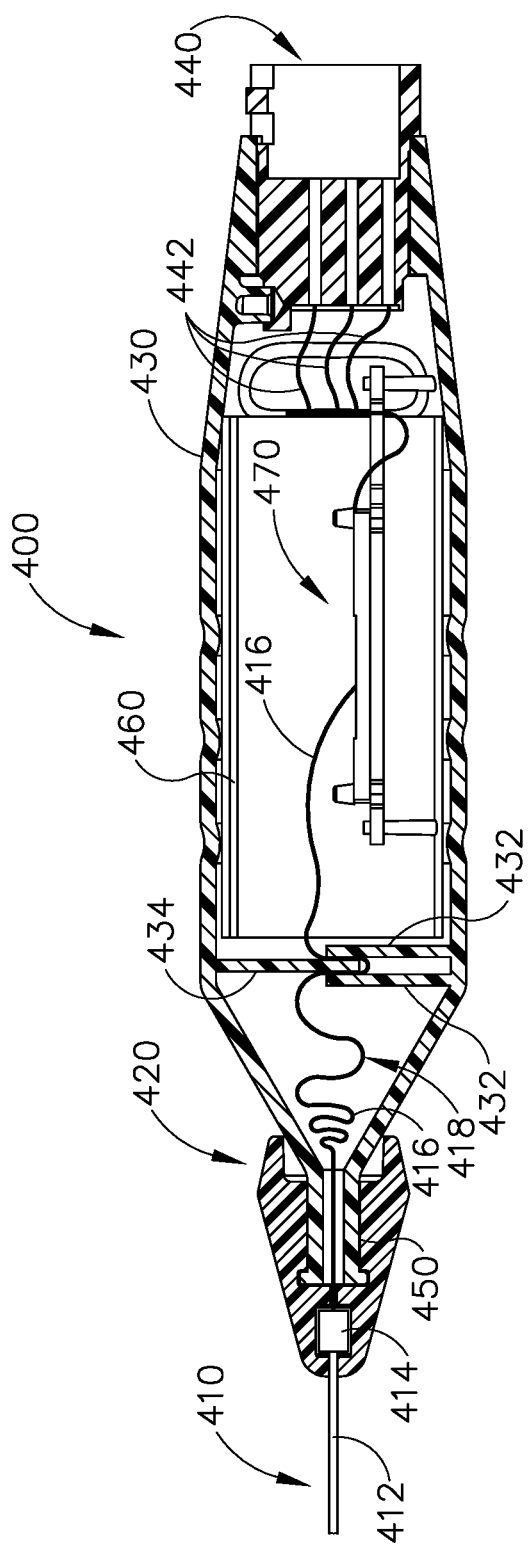
FIG. 18 depicts a cross-sectional side view of the coupling assembly and navigational guidewire of FIG. 15.
Figure 19:
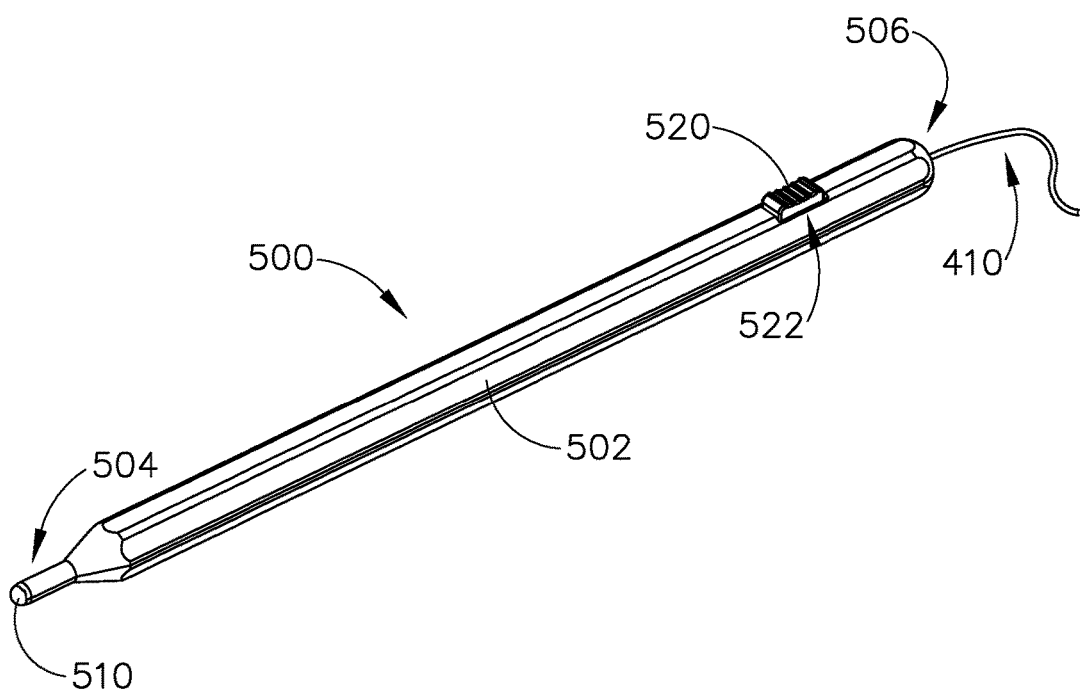
FIG. 19 depicts a perspective view of an exemplary navigation system registration instrument.

Coupling assembly (400) of this example comprises a body (430) and a ferrule (420) located at the distal end of body (430). As best seen in FIGS. 16 and 18, the proximal end of body (430) defines a socket (440) that is configured to receive a plug of coupling unit (132). As best seen in FIGS. 17-18, the distal end of body (430) includes a cylindraceous projection (450) that receives ferrule (420). Projection (450) includes an annular flange (452) and defines an opening (454) that is sized to slidably receive navigation cable (416) of navigational guidewire (410). Opening (454) is further sized to enable rotation of navigation cable (416) within projection (450).

Ferrule (420) comprises a lower body (422) and an upper body (424). Bodies (422, 424) each define a first recess (426) and a second recess (428). First recesses (426) are together configured to receive anchor (414). By way of example only, anchor (414) may be fixedly adhered within recesses (426), thereby providing a unitary coupling between anchor (414) and ferrule (420). Recesses (428) are configured to rotatably receive projection (450). Ferrule (420) is thus operable to freely rotate about projection (450). However, flange (452) is configured to prevent ferrule (420) from moving longitudinally relative to body (430). In some versions, a heat shrink wrap extends from a distal portion of ferrule (420) to a proximal portion of navigational guidewire (410) that extends distally from ferrule (420). In addition or in the alternative, a strain relief boot or other strain relief feature may be positioned over a distal portion of ferrule (420) and the proximal portion of navigational guidewire (410) that extends distally from ferrule (420).

As shown in FIG. 18, navigation cable (416) passes freely through the interior of projection (450) and further into the larger hollow interior of body (430). Navigation cable (416) forms a service loop (418) in the hollow interior of body (430) before reaching a set of bosses (432, 434). Bosses (432, 434) project laterally within the hollow interior of body (430) and have free ends that overlap along the longitudinal axis of body (430). Bosses (432, 434) are positioned adjacent to each other to capture navigation cable (416). In particular, bosses (432, 434) deflect navigation cable (416) along a tortuous path, providing friction therealong to prevent the captured length of navigation cable (416) from translating within body (430). While bosses (432, 434) are used to restrict longitudinal movement of navigation cable (416) within body (430) in the present example, it should be understood that other features may be used to restrict longitudinal movement of navigation cable (416) within body (430).

Navigation cable (416) continues proximally past bosses (432, 434) and is then coupled with a circuit board (470). Circuit board (470) is also coupled with socket (440) via wires (442). Circuit board (470) and wires (442) thus provide a communicative interface from navigation cable (416) to socket (440). As is also shown in FIG. 18, a magnetic shield (460) is positioned around circuit board (470) and a portion of the length of navigation cable (416). Magnetic shield (460) is configured to prevent interference or noise in the signal communicated through coupling assembly (400). By way of example only, magnetic shield (460) may be formed of mu-metal (a nickel-iron soft magnetic alloy with high permeability). Other suitable materials that may be used to form magnetic shield (460) will be apparent to those of ordinary skill in the art in view of the teachings herein.

It should be understood from the foregoing that coupling assembly (400) may enable navigational guidewire (410) to be freely rotated during use of navigational guidewire (410) in a surgical procedure, without meaningfully risking the integrity of the coupling between navigation cable (416) and coupling unit (132). Ferrule (420) allows outer coil (412) to rotate freely relative to body (430). Service loop (418) allows navigation cable (416) to rotate freely relative to body (430). In particular, if the operator rotates navigational guidewire (410) during use of navigational guidewire (410) in a surgical procedure, navigation cable (416) will rotate freely within body (430) along service loop (418). During normal rotation of navigational guidewire (410) in a surgical procedure, the slackness in service loop (418) will allow navigation cable (416) to twist without binding or compromising the integrity of navigation cable (416). To the extent that navigation cable (416) may eventually bind upon excessive twisting from excessive rotation of navigational guidewire (410), an operator would need to rotate navigational guidewire (410) excessively far beyond that which would be encountered during normal use of guidewire (1410) in order for navigation cable (416) to bind.

In addition to preserving the integrity of navigation cable (416) and the connection of navigation cable (416) with circuit board (470), the configuration of coupling assembly (400) and service loop (418) may prevent the operator from encountering rotational drag as the operator rotates navigational guidewire (410) during normal use of navigational guidewire (410).

V. EXEMPLARY INSTRUMENT TO REGISTER AND CALIBRATE IMAGE GUIDED SURGERY NAVIGATION SYSTEM

As noted above, a navigational guidewire such as any of the guidewires (130, 200, 250, 410) described herein may be used to perform registration and calibration in an IGS navigation system (100). Such guidewires may be rather flimsy or flexible by their very nature. This flimsiness flexibility may make it difficult for an operator to grasp the guidewire by itself and manipulate the distal tip of the guidewire to contact the registration points (310, 352, 346) on the patient's head. For instance, the distal tip of the guidewire may tend to deflect in response to engagement with the patient's head, which may compromise the accuracy of the registration. It may therefore be desirable to at least temporarily provide rigidity to a guidewire such as any of the guidewires (130, 200, 250, 410) described herein during the process of registration and calibration in an IGS navigation system (100). Such added rigidity may make it easier for the operator to handle the guidewire, may prevent the distal tip of the guidewire from deflecting in response to engagement with the patient's head, and may ultimately provide a more accurate registration.

Figure 20:
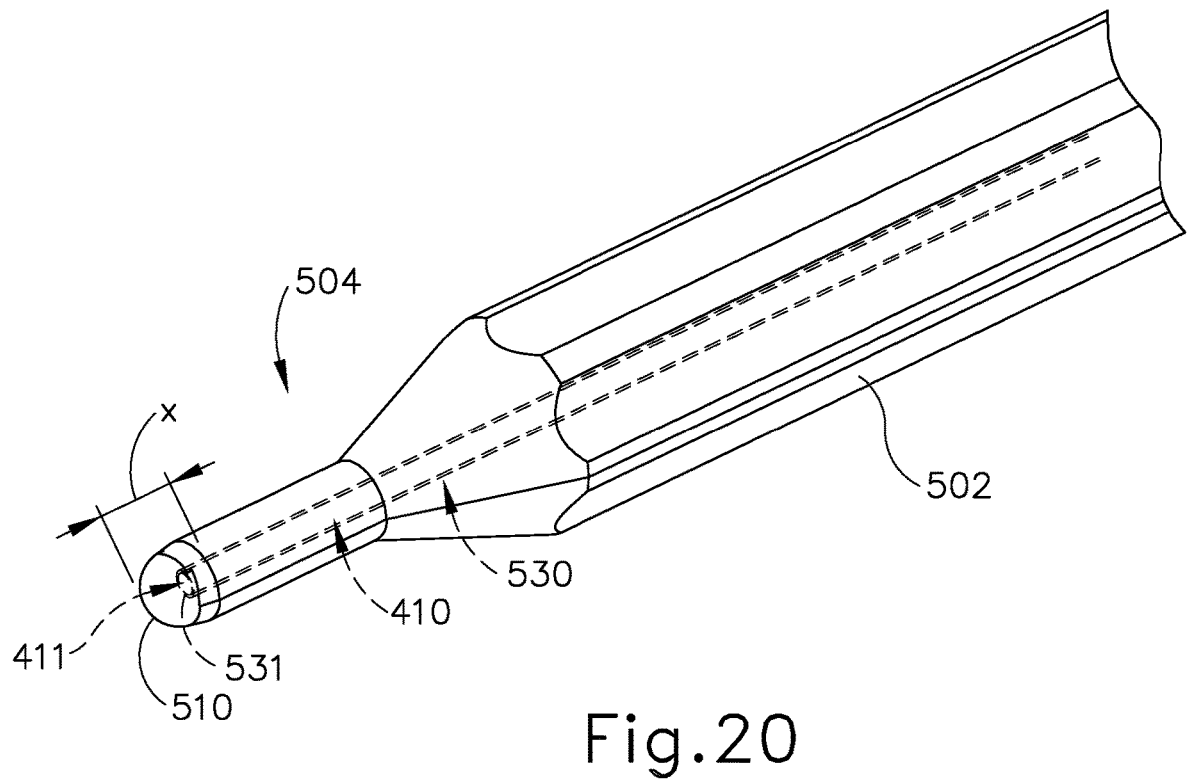
FIG. 20 depicts an enlarged perspective view of the distal end of the instrument of FIG. 19.
Figure 21A:
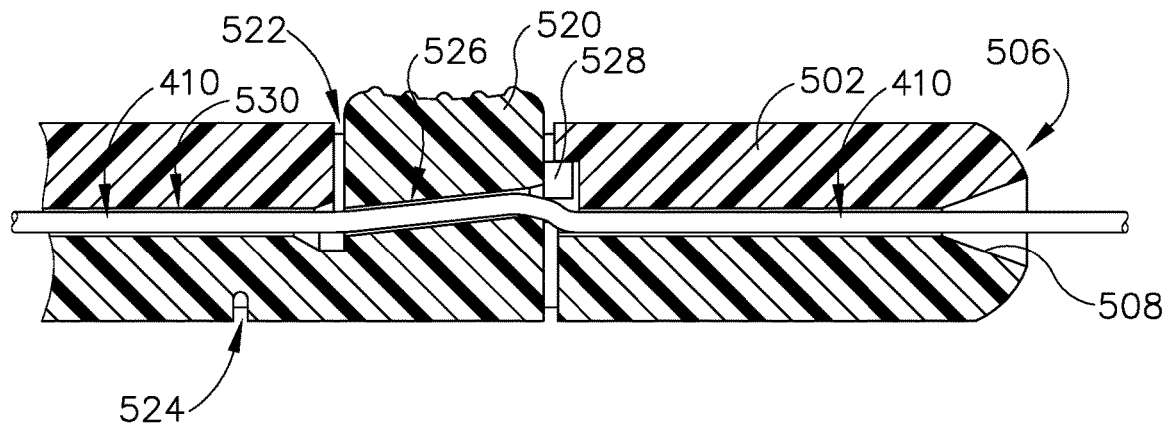
FIG. 21A depicts a cross-sectional side view of a proximal portion of the instrument of FIG. 19, with the navigational guidewire of FIG. 15 secured in the instrument by a retention feature.
Figure 21B:
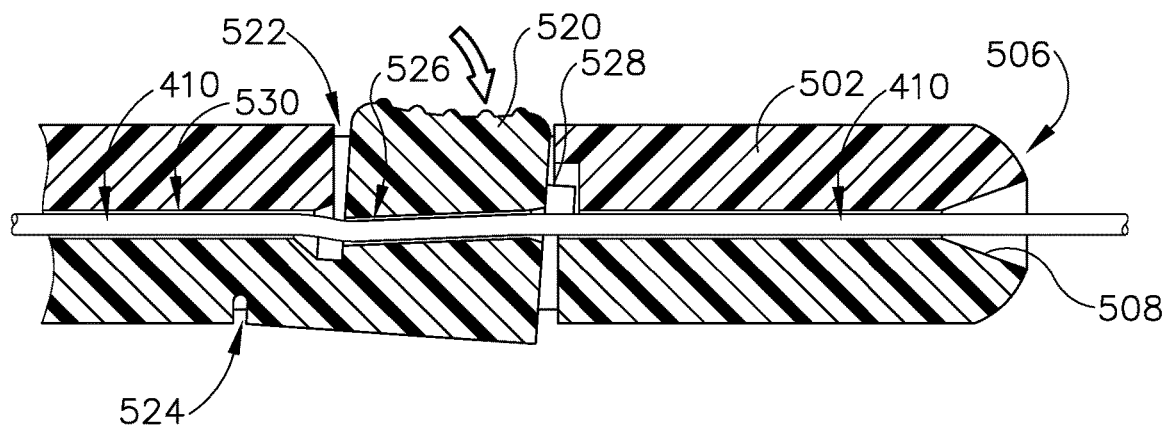
FIG. 21B depicts a cross-sectional side view of a proximal portion of the instrument of FIG. 19, with the retention feature deflected to release the navigational guidewire.
Figure 21C:
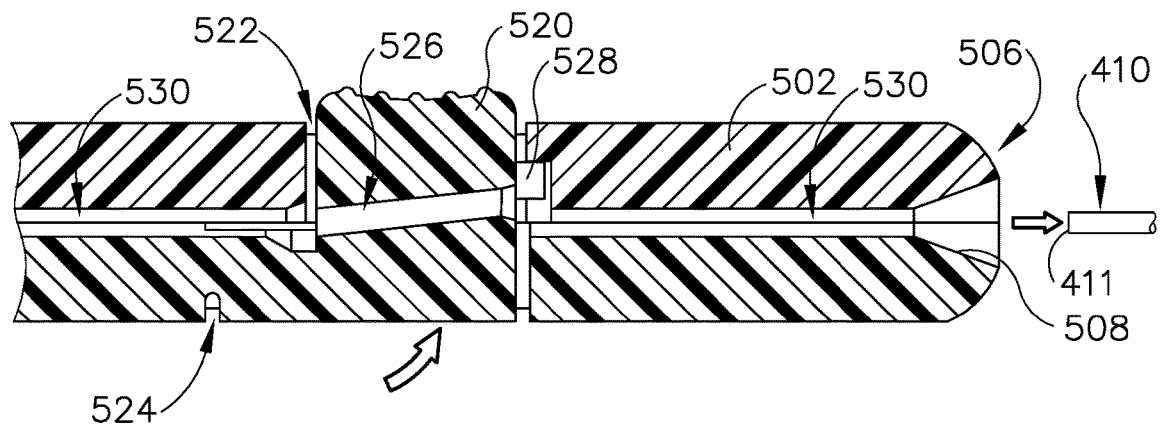
FIG. 21C depicts a cross-sectional side view of a proximal portion of the instrument of FIG. 19, with the navigational guidewire removed from the instrument, and with the retention feature returned to the position of FIG. 21A.

FIGS. 19-21C show an exemplary calibration instrument (500) that may be used to temporarily provide rigidity to an otherwise flimsy guidewire in order to register and calibrate an IGS navigation system such as IGS navigation system (100) described above. Calibration instrument (500) of this example comprises a rigid elongate body (502) having a distal end (504) and a proximal end (506). In some versions, elongate body (502) is formed of a transparent polycarbonate material. As best seen in FIG. 20, distal end (504) includes a taper leading to a reduced diameter portion, which ultimately terminates in a rounded distal tip (510). Distal tip (510) is closed in this example. As shown in FIGS. 21A-21C, proximal end (506) is opening. In particular, proximal end (506) includes a frustoconical channel (508) leading to a lumen (530) within body (502). As shown in FIG. 20, lumen (530) distally terminates in a distal end (531) that is just proximal to distal tip (510). In particular, distal end (531) is proximally spaced from distal tip (510) by a distance (x). By way of example only, this distance (x) may be 1 mm.

Lumen (430) is configured to slidably receive navigational guidewire (410). When navigational guidewire (410) is fully inserted in lumen (430), the distal tip (411) of guidewire (410) abuts distal end (531) of lumen (530). Thus, distal tip (411) is separated from distal tip (510) by a known distance (x). In versions where body (502) is transparent (or at least where distal end (504) is transparent), the operator may visually inspect distal end (504) to confirm that navigational guidewire (410) is fully inserted in lumen (430) such that distal tip (411) abuts distal end (531). If necessary, the operator may advance navigational guidewire (410) further distally until distal tip (411) abuts distal end (531).

Instrument (500) further includes a locking button (520) that protrudes laterally through an opening (522) formed in body (502). As shown in FIGS. 21A-21C, locking button (520) is pivotably coupled with body (502) by a living hinge (524). Locking button (520) further includes a lumen (526) and a proximally extending tab (528). Tab (528) is configured to engage corresponding regions of body (502) to restrict pivotal movement of locking button (520) at living hinge (524). Lumen (526) will either be mis-aligned or substantially aligned with lumen (530) based on the pivotal position of locking button (520). In particular, lumen (526) is mis-aligned with lumen (530) when locking button (520) is in the position shown in FIGS. 21A and 21C; and is substantially aligned with lumen (530) when locking button (520) is in the position shown in FIG. 21B. Lumen (526) has a diameter that complements the diameter of lumen (530), such that lumen (526) is also configured to slidably receive navigational guidewire (410).

When navigational guidewire (410) is disposed in lumens (526, 530) in the arrangement shown in FIG. 21A, the misalignment of lumens (526, 530) forces navigational guidewire (410) to contort and thereby engage edges of body (502) and locking button (520). This provides friction that substantially secures the longitudinal position of navigational guidewire (410) relative to body (502). Navigational guidewire (410) is thus substantially locked in place in the arrangement shown in FIG. 21A. In this configuration, instrument (500) may be used to perform the registration and calibration process associated with IGS navigation system (100) as described above. During the associated movement of instrument (500), the frustoconical configuration of channel (508) may prevent damage to the portion of navigational guidewire (410) exiting body (502). It should also be understood that while distal tip (510) will be contacting the registration points (310, 352, 346) on the patient's head instead of distal tip (411) contacting those registration points (310, 352, 346), processor (110) may readily make the necessary adjustments in the registration and calibration algorithms in view of the fact that the distance (x) between distal tips (411, 510) is fixed and known.

Upon completing the registration and calibration process, the operator may wish to remove navigational guidewire (410) from body (502) In order to use navigational guidewire (410) in a surgical procedure. In order to unlock navigational guidewire (410) from body (502), the operator may press laterally on locking button (520) to deflect locking button (520) to the position shown in FIG. 21B. This will substantially align lumen (526) with lumen (530). With lumens (526, 530) substantially aligned, the friction that was previously provided by corresponding edges of body (502) and locking button (520) is relieved, thereby allowing navigational guidewire (410) to be freely pulled proximally from body (502) while locking button (520) is depressed. In some versions, locking button (520) is configured to fully align lumen (526) with lumen (530) when locking button (520) is fully depressed. In some other versions, locking button (520) does not fully align lumen (526) with lumen (530) when locking button (520) is fully depressed, but lumens (526, 530) are aligned enough to enable navigational guidewire (410) to be pulled proximally from body (502) without damaging navigational guidewire (410). Lumens (526, 530) may thus be "substantially aligned" when locking button (520) is fully depressed.

After navigational guidewire (410) has been pulled free of body (502), the operator may release locking button (520). In response, the resilience of living hinge (524) may drive locking button (520) back to the locking position as shown in FIG. 21C. Body (502) may then be discarded or processed for re-use in a subsequent registration and calibration process. Navigational guidewire (410) may then be used in a surgical procedure in combination with IGS navigation system (100) and other instrumentation. In the event that an operator later wishes to insert another navigational guidewire (410) into body (502), the operator may hold locking button (520) in a depressed state, insert navigational guidewire (410) along lumens (526, 530) until distal tip (411) engages distal end (531), then release locking button (520) to lock navigational guidewire (410) in place within body (502).

In some instances, instrument (500) may be provided in a sealed, sterile package with guidewire (410) already inserted in body (502) and locked by locking button (520). This may prevent the operator from having to load navigational guidewire (410) into body (502) before using instrument (500) in the registration and calibration process. This may also enable body (502) to serve as a protective barrier that prevents the sterile distal end of navigational guidewire (410) from being contaminated during the registration and calibration process.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a navigational guidewire, wherein the navigational guidewire comprises: (i) a sensing element, wherein the sensing element is configured to respond to positioning within an electromagnetic field, (ii) an outer member, and (iii) a conductor extending along the length of the outer member, wherein the conductor is in communication with the sensing element; (b) a connector assembly, wherein the connector assembly is configured to couple the navigational guidewire with a navigation system, wherein the connector assembly comprises: (i) a body, and (ii) a ferrule coupled with the body, wherein the navigational guidewire is coupled with the ferrule, wherein the ferrule is rotatable relative to the body to thereby enable rotation of the navigational guidewire relative to the body.

Example 2

The apparatus of Example 1, wherein the navigational guidewire further includes an anchor member, wherein the anchor member secures the navigational guidewire to the ferrule.

Example 3

The apparatus of Example 2, wherein the anchor is secured to a proximal end of the outer member of the navigational guidewire.

Example 4

The apparatus of Example 3, wherein the conductor extends proximally from the outer member.

Example 5

The apparatus of Example 4, wherein the outer member proximally terminates in the ferrule.

Example 6

The apparatus of Example 5, wherein the conductor extends proximally past the ferrule and into the body.

Example 7

The apparatus of any one or more of Examples 1 through 6, wherein the conductor comprises a conductive wire.

Example 8

The apparatus of any one or more of Examples 1 through 7, wherein the body includes a distal projection, wherein the ferrule is coupled with the distal projection.

Example 9

The apparatus of Example 8, wherein the distal projection includes an annular flange received in the ferrule, wherein the annular flange is configured to prevent longitudinal movement of the ferrule relative to the body.

Example 10

The apparatus of any one or more of Examples 8 through 9, wherein the distal projection defines an opening, wherein the conductor passes through the opening and into a hollow interior of the body.

Example 11

The apparatus of any one or more of Examples 1 through 10, wherein the body defines a hollow interior, wherein the conductor extends into the hollow interior.

Example 12

The apparatus of Example 11, wherein the conductor forms a service loop in the hollow interior.

Example 13

The apparatus of Example 12, wherein the body further includes a plurality of bosses extending into the hollow interior, wherein the bosses are configured to capture the conductor and thereby prevent movement of at least a portion of the conductor within the hollow interior.

Example 14

The apparatus of any one or more of Examples 1 through 13, wherein the connector assembly further comprises a magnetic shield.

Example 15

The apparatus of any one or more of Examples 1 through 14, wherein the connector assembly further comprises a socket, wherein the socket is configured to receive a plug from a navigation system, wherein the connector assembly is configured to provide communication between the conductor and the socket.

Example 16

An apparatus, comprising: (a) a rigid elongate body, wherein the rigid elongate body defines a lumen; (b) a navigational guidewire disposed in the lumen, wherein the navigational guidewire comprises a sensing element, wherein the sensing element is configured to respond to positioning within an electromagnetic field; and (c) a locking element, wherein the locking element is configured to selectively lock the navigational guidewire in the lumen.

Example 17

The apparatus of Example 16, wherein the rigid elongate body has an open proximal end and a closed distal end, wherein the lumen extends from the open proximal end of the body to a closed lumen end, wherein the closed lumen end is proximal to the closed distal end of the elongate body, wherein the navigational guidewire has a distal tip abutting the closed lumen end.

Example 18

The apparatus of any one or more of Examples 17 through 18, wherein the locking element comprises a resiliently biased button having a lumen segment, wherein the button is operable to transition between a locking position and an unlocking position, wherein the lumen segment is configured to be misaligned with the lumen of the rigid elongate body when the button is in the locking position, wherein the lumen segment is configured to be substantially aligned with the lumen of the rigid elongate body when the button is in the unlocking position.

Example 19

The apparatus of any one or more of Examples 16 through 18, wherein at least a distal portion of the rigid elongate body is transparent to enable visualization of a distal end of the navigational guidewire in the lumen.

Example 20

A method comprising: (a) manipulating a distal tip of an instrument to contact a plurality of registration points on a patient's face within an electromagnetic field to thereby calibrate an image guided surgery navigation system, wherein the instrument comprises: (i) a rigid elongate body having a distal tip, and (ii) a navigational guidewire inserted in the rigid elongate body, wherein the navigational guidewire has a distal tip containing a sensing coil, wherein the distal tip of the navigational guidewire is proximal to the distal tip of the rigid elongate body, wherein the sensing coil provides position indicative signals to the image guided surgery navigation system during the act of manipulating the distal tip of the instrument; (b) removing the navigational guidewire from the rigid elongate body; and (c) using the navigational guidewire in a surgical procedure with the image guided surgery navigation system.

VII. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. An apparatus comprising:
  (a) a navigational guidewire, wherein the navigational guidewire comprises:
    (i) a sensing element, wherein the sensing element is configured to respond to positioning within an electromagnetic field,
    (ii) an outer member,
    (iii) a conductor extending along the length of the outer member, wherein the conductor is in communication with the sensing element, and
    (iv) an anchor member secured to a proximal end of the outer member;

(b) a connector assembly, wherein the connector assembly is configured to couple the navigational guidewire with a navigation system, wherein the connector assembly comprises:
   (i) a body, and
   (ii) a ferrule coupled with the body, wherein the navigational guidewire is coupled with the ferrule via the anchor member, wherein the ferrule is rotatable relative to the body to thereby enable rotation of the navigational guidewire relative to the body.

2. The apparatus of claim 1, wherein the conductor extends proximally from the outer member.

3. The apparatus of claim 2, wherein the outer member proximally terminates in the ferrule.

4. The apparatus of claim 3, wherein the conductor extends proximally past the ferrule and into the body.

5. The apparatus of claim 1, wherein the conductor comprises a conductive wire.

6. The apparatus of claim 1, wherein the body includes a distal projection, wherein the ferrule is coupled with the distal projection.

7. The apparatus of claim 6, wherein the distal projection includes an annular flange received in the ferrule, wherein the annular flange is configured to prevent longitudinal movement of the ferrule relative to the body.

8. The apparatus of claim 6, wherein the distal projection defines an opening, wherein the conductor passes through the opening and into a hollow interior of the body.

9. The apparatus of claim 1, wherein the body defines a hollow interior, wherein the conductor extends into the hollow interior.

10. The apparatus of claim 9, wherein the conductor forms a service loop in the hollow interior.

11. The apparatus of claim 10, wherein the body further includes a plurality of bosses extending into the hollow interior, wherein the bosses are configured to capture the conductor and thereby prevent movement of at least a portion of the conductor within the hollow interior.

12. The apparatus of claim 1, wherein the connector assembly further comprises a magnetic shield.

13. The apparatus of claim 1, wherein the connector assembly further comprises a socket, wherein the socket is configured to receive a plug from a navigation system, wherein the connector assembly is configured to provide communication between the conductor and the socket.

14. An apparatus comprising:
(a) a navigational guidewire, wherein the navigational guidewire comprises:
   (i) a sensing element, wherein the sensing element is configured to respond to positioning within an electromagnetic field,
   (ii) an outer member,
   (iii) a conductor extending along the length of the outer member, wherein the conductor is in communication with the sensing element;
(b) a connector assembly, wherein the connector assembly is configured to couple the navigational guidewire with a navigation system, wherein the connector assembly comprises:
   (i) a body, wherein the body includes a distal projection having an annular flange, and
   (ii) a ferrule coupled with the annular flange, wherein the annular flange is configured to prevent longitudinal movement of the ferrule relative to the body, wherein the navigational guidewire is coupled with the ferrule, wherein the ferrule is rotatable relative to the body to thereby enable rotation of the navigational guidewire relative to the body.

15. The apparatus of claim 14, wherein the conductor extends proximally from the outer member.

16. The apparatus of claim 15, wherein the outer member proximally terminates in the ferrule.

17. The apparatus of claim 14, wherein the conductor comprises a conductive wire.

18. An apparatus comprising:
(a) a navigational guidewire, wherein the navigational guidewire comprises:
   (i) a sensing element, wherein the sensing element is configured to respond to positioning within an electromagnetic field,
   (ii) an outer member,
   (iii) a conductor extending along the length of the outer member, wherein the conductor is in communication with the sensing element;
(b) a connector assembly, wherein the connector assembly is configured to couple the navigational guidewire with a navigation system, wherein the connector assembly comprises:
   (i) a body,
   (ii) a ferrule coupled with the body, wherein the navigational guidewire is coupled with the ferrule, wherein the ferrule is rotatable relative to the body to thereby enable rotation of the navigational guidewire relative to the body, and
   (iii) a socket, wherein the socket is configured to receive a plug from a navigation system, wherein the connector assembly is configured to provide communication between the conductor and the socket.

19. The apparatus of claim 18, wherein the body defines a hollow interior, wherein the conductor extends into the hollow interior.

20. The apparatus of claim 18, wherein the connector assembly further comprises a magnetic shield.

* * * * *